United States Patent [19]

Manning et al.

[11] Patent Number: 5,066,596
[45] Date of Patent: Nov. 19, 1991

[54] **BACTERIAL STRAINS HARBORING CLONED GENES CONTROLLING *VIBRIO CHOLERAE* O-ANTIGEN BIOSYNTHESIS**

[75] Inventors: Paul A. Manning, Flagstaff Hill; Peter R. Reeves, Hawthorndene; Derrick Rowley, Beaumont, all of Australia

[73] Assignee: Enterovax Limited, North Adelaide, Australia

[21] Appl. No.: 80,362

[22] Filed: Jul. 31, 1987

Related U.S. Application Data

[63] Continuation-in-part of Ser. No. 782,720, Sep. 30, 1985, abandoned.

[30] Foreign Application Priority Data

Feb. 1, 1984 [AU] Australia .................... PG3423
Nov. 2, 1984 [AU] Australia .................... PG7958
Jan. 31, 1985 [WO] PCT Int'l Appl. ............. PCT/AU85/00015

[51] Int. Cl.$^5$ .............. C12N 1/21; C12N 15/09; C12N 15/31; C12N 15/63; A61K 39/02
[52] U.S. Cl. .................. 435/252.33; 435/69.1; 435/69.3; 435/91; 435/172.1; 435/172.3; 435/320.1; 435/848; 536/27; 935/6; 935/9; 935/22; 935/26; 935/60; 935/73; 424/92
[58] Field of Search .......... 435/69.1, 69.3, 91, 435/172.3, 252.33, 172.1, 320, 848; 536/27; 935/6, 9, 22, 26, 60, 73; 424/92

[56] References Cited

U.S. PATENT DOCUMENTS

| | | | |
|---|---|---|---|
| 3,856,935 | 12/1974 | Germanier | 424/92 |
| 4,264,737 | 4/1981 | Murphy | 435/172.1 |
| 4,311,797 | 1/1982 | Khachatourians | 435/172.1 |
| 4,440,748 | 4/1984 | Graham | 424/92 |

FOREIGN PATENT DOCUMENTS

| | | |
|---|---|---|
| 0080806 | 3/1981 | European Pat. Off. . |
| 0087735 | 6/1982 | European Pat. Off. . |
| 0084522 | 9/1983 | European Pat. Off. . |
| 0018154 | 5/1984 | European Pat. Off. . |
| 0095452 | 6/1984 | European Pat. Off. . |
| 0127153 | 5/1985 | European Pat. Off. . |
| WO82/03088 | 10/1982 | PCT Int'l Appl. . |
| WO83/00437 | 10/1983 | PCT Int'l Appl. . |
| 2094314 | 9/1981 | United Kingdom . |
| 209314 | 4/1982 | United Kingdom . |
| 1472624 | 5/1983 | United Kingdom . |
| 2076287 | 7/1984 | United Kingdom . |

OTHER PUBLICATIONS

Formai et al., "Construction of a Potential Bivalent Vaccine Strain: Introduction of Shigella Sonnei Form I Antigen Genes into the gale Salmonella Typhi Ty21a Typhoid Vaccine Strain", Infection and Immunity, 34(3), Dec. 1981, 746–750.

Shipley et al., "Identification and Cloning of the Genetic Determinant that Endcodes for the K88ac Adherence Antigen", J. Bacteriol: 145(2), Feb. 1981: 920–925.

Embden et al., "Cloning and Expression of a Deoxyribonucleic Acid Fragment that Encodes for the Adhesive Antigen K99", Infect. Immun., 29(3), Sep. 1980: 1125–1113.

Maniatis et al., Molecular Cloning (Cold Springs: Cold Springs Harbor Laboratory, 1982), 85, 284, 295 and 298.

Clements et al., discloses "Construction of a Potential Live Oral Bivalent Vaccine for Typhoid Fever and Cholera-*Eschericia coli*-Related Diarrheas", Infection and Immunity, 46(2), Nov. 1984: 564–569.

(List continued on next page.)

Primary Examiner—Richard A. Schwartz
Assistant Examiner—Richard C. Peet
Attorney, Agent, or Firm—Iver P. Cooper

[57] ABSTRACT

The invention relates to a fragment of DNA containing genes encoding the synthesis of the O-antigen of *Vibrio cholerae* serotypes Inaba or Ogawa and being at least 16 kb in length. The invention further related to a cosmid comprising a cloned DNA fragment containing genes encoding the synthesis of O-antigen of *Vibrio cholerae* serotypes Inaba or Ogawa and to a strain of *E.coli* that includes the fragment.

16 Claims, 33 Drawing Sheets

OTHER PUBLICATIONS

Hohmann et al., discloses "Intestinal and Serum Antibody Responses in Mice After Oral Immunization with Salmonella, E. coli, and Salmonella E. coli Hybrid Strains", Infection and Immunity, 25(1), Jul. 1979: 27-33.

Mullany et al., "Expression of Plasmids Coding for Colonization Factor Antigen II (CFA/II) and Enterotoxin Production in Escherichia coli", J. Gen. Microbiol., 129, (1983), 3591-3601.

Mekalanos et al., "Cholera Toxin Genes: Nucleotide Sequence, Deletion Analysis and Vaccine Development", Nature, (306), Dec. 1983: 551-557.

Smirnova, "Primary Mapping of the oag Locus Determining Somatic O Antigen Synthesis on the Chromosome of Vibrio eltor", Chem. Abs., 76(7), 1983: 48846.

Chem. Abs., vol. 98, No. 11, 14th Mar. 1983, p. 137, Abst. No. 84368K, Columbus, Ohio, discloses an article by G. Willshaw et al., "Cloning of Regions Encoding Colonization Factor Antigen 1 and Heat-Stable Enterotoxin in Escherichia coli", FEMS Microbial. Lett., 1983, 16(1), 101-106.

Feiss et al. discloses "Isolation of Plaque-Forming Galactose-Transducing Strains of Phage Lambda", Genetics, (1972), 71:189-206.

Germanier et al., "Characteristics of the Attenuated Oral Vaccine Strain 'S. Typhi' TY21a", Develop. Biol. Standard, (1983), 53:3-7.

Collins et al., "Infection-Immunity in Experimental Salmonelosis", (1966), pp. 601-619, Trudeau Institute.

Shapiro et al. discloses "The Galactose Operon of E. coli K-12. A Deletion Analysis of Operon Structure and Polarity", Genetics, (1969), 62:249-261.

Fukasawa et al., discloses "Galactose Mutants of Salmonella typhimurium", Genetics, (1961), 46:1295-1303.

Fukasawa et al., discloses "Galactose-Sensitivity Mutants of Salmonella", Biochem. Biophys. Acctg., (1961), 48:470-483.

Germanier discloses, "Immunity in Experimental Salmone-losis", Infection and Immunity, (1970), 2(3):309-315.

Germanier et al., discloses "Immunity in Experimental Salmonellosis", Infection and Immunity, (1972), 5(5):792-797.

Gilman et al., discloses "Evaluation of a VDP--Glucose-4 Epimeraseless Mutant of Salmonella typhi as a Live Oral Vaccine", (1977), 136(6):717-723, J. of Infectious Diseases.

Nikaido discloses "Galactose-Sensitive Mutants of Salmonella", Biochem. Biophys. Acctg., (1961), 48:460-469.

Blanden et al., discloses "Mechanisms of Acquired Resistance in Mouse Typhoid", (1966), pp. 585-600, Trudeau Institute.

Collins et al., discloses "Comparative Immunogenicity of Heat-Killed and Living Oral Salmonella Vaccines", Infection and Immunity, (1972), 6(4):451-458.

Mackaness et al., "Hot-Parasite Relations in Mouse Typhoid", pp. 573-583, Trudeau Institute.

Germanier discloses "Typhoid Fever", Bacterial Vaccines, Academic Press, Inc., (1984), pp. 137-165.

Bachmann et al., discloses "Linkage Map of Escherichia coli K-12, Edition 6", Microbiological Reviews, (1980), 44(1):1-56.

Germanier et al., discloses "Immunity in Experimental Salmonellosis, II, Basic for the Avirulence and Protective Capacity of galE Mutants", Immunity and Infection, vol. 4, No. 6, Dec. 1971, pp. 663-673.

Black et al., discloses "Immunogenicity of Ty21a Attenuated Salmonella Typhi Given with Sodium Bicarbonate or in Enteric Coated Capsules", Develop. Biol. Standard, vol. 53, pp. 9-14, 1983.

Linde, discloses "Stable, Highly Immunogenic Mutants of Salmonella with Two Independent, Attenuating Markers as Potential Live Vaccine and Their Validity for Shigella and Other Bacteria", Develop. Biol. Standard, vol. 53, pp. 15-28, 1983.

Chau et al., discloses "Antibody Response to the Protein Antigens of Salmonella typhi During Typhoid Infection and Following Vaccination with a Live Oral Typhoid Vaccine Ty21a".

FIG. II.

VIBRIO CHOLERAE 017
LE 392
LE 392 [pPM 431]

pHC 79
pPM 1001

FIG. 25.

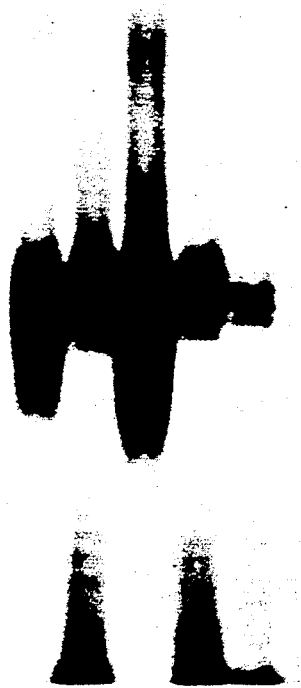
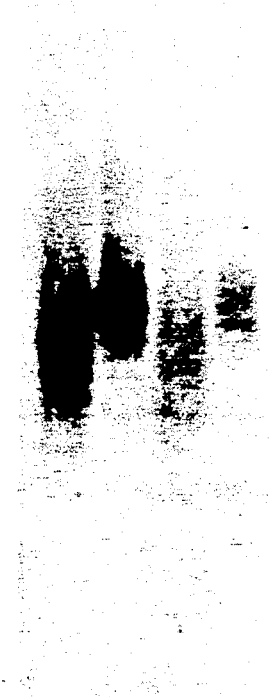
FIG. 28.

BACTERIAL STRAINS HARBORING CLONED GENES CONTROLLING VIBRIO CHOLERAE O-ANTIGEN BIOSYNTHESIS

This application is a continuation-in-part of application Ser. No. 782,720, filed Sept. 30, 1985, abandoned.

This invention relates to bacterial strains which are useful and which are achievable by genetic engineering techniques.

The problem to which this invention at least in its broadest sense can be said to relate is a difficulty associated with providing for effective immunisation against a major category of intestinal pathogens.

Such pathogens can include and are typified by *Vibrio cholerae*.

Bacterial intestinal pathogens fall into two categories. In the first are those which cause their effects by producing a toxin acting on the intestinal epithelial cells whilst the organism itself is confined to and grows in the intestinal lumen: *Vibrio cholerae*, which causes cholera in man, and enterotoxigenic *Escherichia coli*, different strains of which cause diarrhoea in man, swine scours and calf scours all being to this category. In the other division are organisms like Salmonellae which in both man and animals can cause systemic disease in which diarrhoea may be an important component. These organisms penetrate through the wall of the intestine initially into the lymphoid tissue there, known as Peyer's patches; during the incubation phase they grow inside these sites and may either be eliminated as a subclinical infection or may lead to overt disease during which they may spread through the bloodstream beyond the intestinal sites.

Those organisms in the first category can be resisted by hosts possessing specific antibodies if these are secreted into the intestinal tract and indeed recovery from infection is usually accompanied by reasonable amounts of intestinal antibody for short periods. With Salmonellae possession of specific antibody is by itself not sufficient to confer immunity; other cellular changes must occur as well. Nevertheless, probably due to their ability to multiply and colonise Peyer's patches, these organisms provoke much better antibody responses of the secretory IgA type than any of those of the former, non-penetrating kind. Using animal models, we have shown that hybrid organisms which possess basically the Salmonella genome plus a small piece specifying the antigenic structure of organisms of the second category behave fundamentally like native Salmonellae when given by mouth: they penetrate and colonise Peyer's patches temporarily and stimulate very good local IgA antibody responses measurable in the intestinal fluid: this antibody response includes one against the introduced antigen.

Vaccine strains according to this invention therefore combine the immunogenic potential of organisms of the first category typified by Salmonellae, with the desired antigens of organisms of the second category, typified by *Vibrio cholerae*.

Hitherto, with the notable exception of live oral polio vaccine most effective vaccines which have been used and proposed involve the intramuscular route.

With reference to *Vibrio cholerae*, a mutant strain, Texas Star-SR, U.S. Pat. No. 4,328,290, and similar genetically engineered strains have been proposed for production of live attenuated vaccines which can be administered orally. These strains, however, suffer from certain drawbacks not the least of which is the fact that they cause limited diarrhoea even with all the known toxin genes deleted. Explanations for this residual diarrhoea are that it is caused by other virulence determinants of *V. cholerae* associated with the ability of these organisms to colonize the epithelium of the small bowel or other toxin. This being so the presence of some residual toxicity might be the price to pay for the use of such attenuated strains of enteric organisms if they are to remain effective immunizing agents. In one case of *Vibrio cholerae* some of this residual toxicity may be due to the extracellular haemolysin it produces.

After substantial investigation, we have found that there is advantage in consideration of using a vaccine appropriate for the oral route and by providing through genetic engineering techniques characteristics of a live bacterial strain that will firstly invade, multiply and briefly colonise the lymphoid tissue of the small intestine of mammalian species, and through an introduced gene or genes or parts thereof effect synthesis of an antigen or antigens to produce IgA antibodies, that such an approach has now been found to enable the production of very effective vaccines.

Accordingly, the invention can be said to reside in a bacterial strain characterised by having a gene set substantially derived from a non pathogen or a pathogen rendered non pathogenic and able to invade, multiply and briefly colonise the lymphoid tissue of the small intestine of mammalian species, and having an introduced gene or genes or parts thereof effective to specify synthesis of an antigen or antigens effective to induce production of IgA antibodies into the small intestine and other secretory surfaces.

The lymphoid tissue is typified by the Peyer's patches in the small intestine.

Preferably, the antigen or antigens are such as to induce production of IgA antibodies effective against any of the following genera where this is a pathogen; Escherichia, Rotavirus, Vibrio, Aeromonas and Bordetella.

With the exception of Bordetella, all pathogens of the above listed genera are enteric organisms. All are characterized by a mechanism ofm pathogenesis which involves the prerequisite step of mucosal adherence followed by toxin production, that is, they are not of the penetrating type. Although Bordetella is not a pathogen of the gut, but of the lungs, this invention can provide for protection against pathogens which adhere to any secretory surface. This is because there exists a central pathway by which antigenic stimulation of IgA precursor cells in the Peyer's patches results in the dissemination of sensitized cells to distant mucosal sites, such as the lungs where they can provide effective immunological protection.

A further aspect of this invention is that the stimulation of IgA production provides a means of measuring the immune response generated. Should the introduced genes code for a protective antigen of an invasive organism such as Campylobacter, Salmonellae or Shigella, the production of IgA antibodies directed against the introduced antigen will provide a means of measuring the generated immune response even though the IgA antibodies are not the important protective factor in these cases.

The introduced gene or genes can be either within the chromosome of the bacterial strain or they can be on a plasmid within the bacterial strain.

Preferably, the pathogen rendered non pathogenic is selected from any one of the following, namely, Escherichia, Salmonella or Shigella.

Preferably, the introduced gene or genes specify the synthesis of at least part of the following, namely adhesins, outer membrane proteins or lipopolysaccharides of the pathogen.

Preferably, in one case, the gene or genes specify the synthesis of the K88 antigen of an enterotoxigenic *Escherichia coli.*

Preferably, as an alternative, the introduced genes specify the synthesis of the K99 antigen of an enterotoxigenic *Escherichia coli.*

Preferably, as an alternative, the introduced gene or genes specify the synthesis of one or more of the antigens CS1, CS2 or CS3 of a CFA/II producing enterotoxigenic *Escherichia coli.*

In an alternative arrangement, the genetic material specifies the synthesis of the colonisation factor antigens of enterotoxigenic *Escherichia coli* pathogenic to man.

Preferably, as a further alternative, the genetic material resides in any one of the plasmids pPM440, pPM500, pPM510 or pPM455, which encode genes specifiying outer membrane proteins of *Vibrio cholerae.*

In a further alternative, the introduced genes are effective to synthesize an O-antigen of *Vibrio cholerae.*

The synthesis of an O-antigen of *Vibrio cholerae* has been achieved but has involved particular difficulties which will be discussed later in the specification.

Preferably, the synthesized O-antigen of *Vibrio cholerae* is present on the surface of *Escherichia coli.*

As an alternative, the synthesized O-antigen is present on the surface of Salmonella or Shigella.

Further to the above, it has been observed that some avirulent Salmonellae strains have retained their capacity to invade the lymphoid follicles (Peyer's patches) following oral administration.

Indeed, it has been found that there is a direct correlation between the degree and length of colonisation of the lymphoid follicles by respective Salmonellae strains and their ability to stimulate immunity (refer to Table 1).

TABLE 1

| Immunising Strain | Kaufmann White Antigens | Survival in* Peyer's patches | Intestinal# IgA/ug/ml | % survival challenge *S. typhimurium* |
|---|---|---|---|---|
| (*S. typhimurium/ E. coli* hybrid 885 | 0.8 | + | 75 | 90 |
| *S. salford* | 16 | + | 38 | 90 |
| *S. strasbourg* | 9,46 | + | 10 | 90 |
| *S. budapest* | 1,4,12 | + | 5 | 42 |
| *S. typhimurium* | 1,4,5,12 | − | 2.5 | 27 |
| *S. fridenau* | 13,22 | − | 2.5 | 10 |
| (*E. coli/ S. typhimurium*) hybrid 1142 | 4,5,12 | − | 2.5 | 10 |

*$10^3$ organisms on day 7 after feeding $5 \times 10^8$ bacteria
Against the homologous lipopolysaccharide antigens.

The carrier organism can be typified by galactose epimeraseless Salmonellae, or virulence-plasmidless Shigellae.

The extent of avirulence is one factor only but another of importance is that the strain be able to invade the Peyer's patches in sufficient numbers and once invaded, their colonisation should be limited to only a few days, typically 3 to 10 days. The result of this will be normally that the host will actively mount a long lived immune response which will also clear the organism from the host.

An additional advantage of all these vaccines is that they are simultaneously protective against the bacterial species which is used as the carrier.

Other advantages of bacterial strains, constructed according to this invention and used as the active ingredient in live, oral vaccines are that a single or limited number of doses will be effective, the vaccine strain will be well characterized genetically with no theoretical possibility of reversion to virulence, and the vaccine is suitable for use in both an active and passive immunization program as the IgA antibodies produced can be passed from mother to infant in colostrum and milk.

In a further aspect of the present invention there is provided a fragment of DNA containing genes encoding the synthesis of the O-antigen and being at least 16 kb in length.

Preferably the fragment of DNA is a Sst/SacI of approximately 19 kb in length.

In a further aspect, the present invention provides a cosmid including a) a suitable cosmid cloning vector; and b) a cloned fragment of DNA containing genes encoding the synthesis of O-antigen and being at least 16 kb in length.

Preferably the cosmid cloning vector is cosmid pHC79.

In a preferred form the cloned fragment of DNA is a Sst/SacI fragment of approximately 19 kb in length.

In a further aspect of the present invention there is provided a cosmid selected from the cosmids pPM1001, pPM1002, pPM1003, pPM1004, pPM1005, as hereinbefore described.

In a still further aspect of the present invention there is provided an avirulent strain of *E. coli* including a fragment of DNA containing genes encoding the synthesis of the O-antigen and being at least 16 kb in length.

Preferably the *E. coli* is an *E. coli* K-12 strain.

More preferably the fragment of DNA is a Sst/SacI fragment of approximately 19 kb in length.

In a further aspect of the present invention there is provided a method for preparing an avirulent strain of *E. coli* including a fragment of DNA containing genes encoding the synthesis of the O-antigen which method includes:

providing a sample of *E. coli* strain and cosmid including a suitable cosmid cloning vector and a first cloned fragment of DNA encoding the synthesis of the O-antigen and being at least 16 kb in length; and cloning the fragment of DNA into the *E. coli* strain.

In a still further aspect of the present invention there is provided a vaccine composition including a fragment of DNA containing genes encoding the synthesis of the O-antigen and being at least 16 kb in length.

BRIEF DESCRIPTION OF THE DRAWINGS

Figure 25:
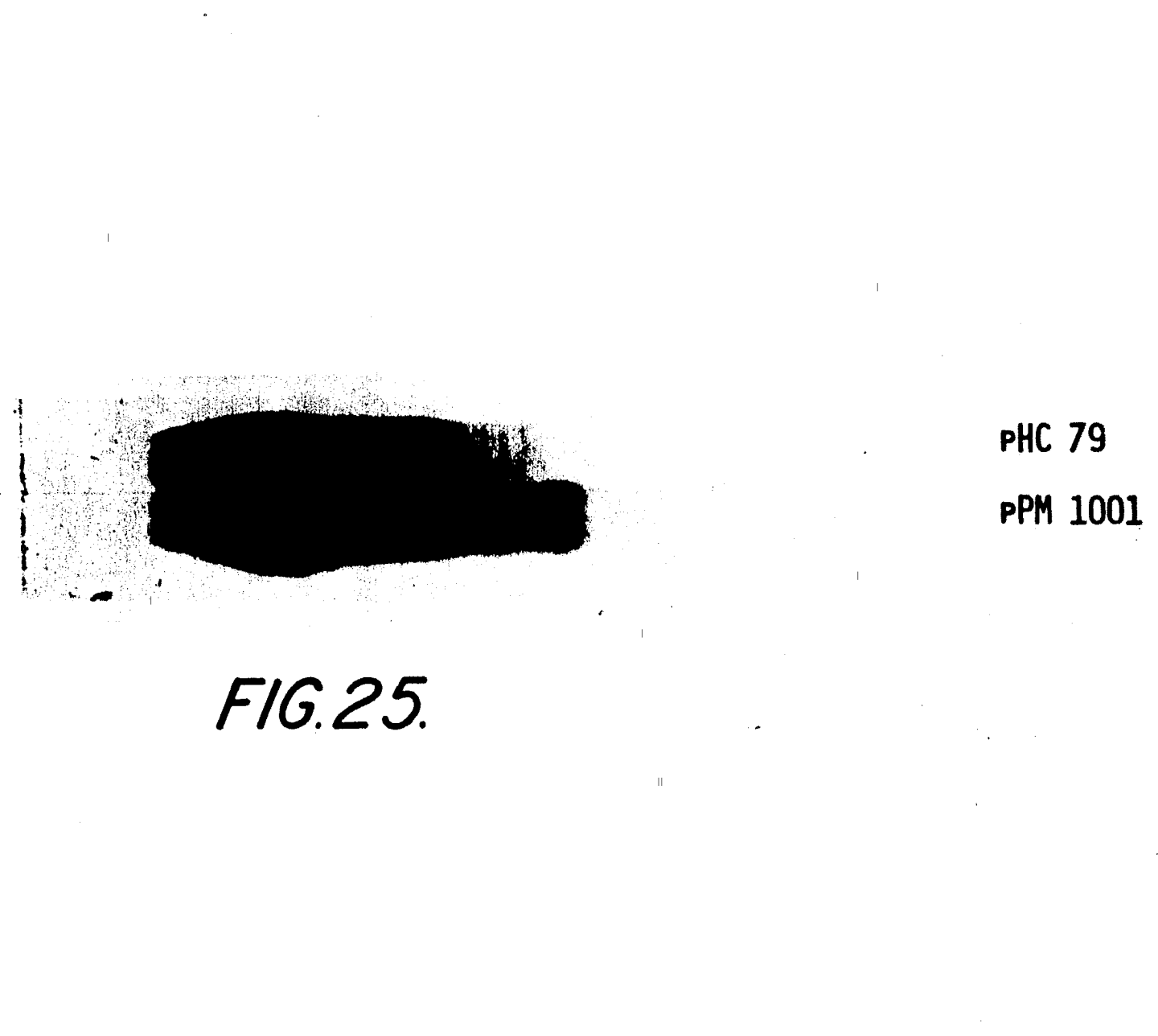

FIG. 25: Purified lipopolysaccharide (LPS) of *E. coli* K-12 strain DH1 with the appropriate plasmids was analyzed by SDS polyacrylamide gel electrophoresis followed by silver staining to visualize the bands.

FIG. 28 presents a photograph of a silver stained gel (panel A) and a nitrocellulose replica (panel B) obtained by a Western blot of a duplicate gel. LPSs from *E. coli* and *V. cholerae* strains were electrophoresed on the gels.

EXAMPLE 1

Figure 1:
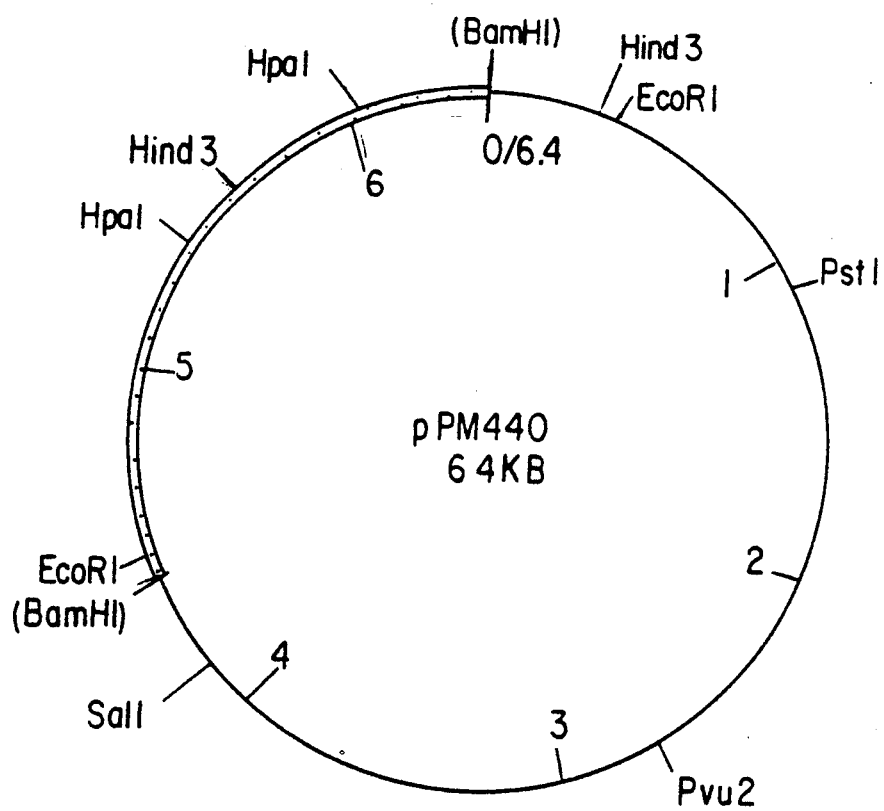
FIG. 1: Restriction map of pPM440.

A live bacterial strain useful as an oral vaccine against scours (enteric colibacillosis) in swine.

One useful vaccine according to this invention is a *Salmonella typhimurium* galactose epimeraseless mutant harbouring a plasmid expressing the K88 antigen of an enterotoxigenic *Escherichia coli*. Such a strain is a useful immunogen to induce the production of gut antibodies to the K88 pilus resulting in protection against the enterotoxigenic *E. coli* K88 strain.

It has been shown that vaccination of a sow with a purified K88 preparation can confer on her offspring passive immunity to a K88 *E. coli*. It could be concluded that antibodies to the K88 antigen in colostrum and milk protect the piglets by neutralization of the adhesive properties due to the K88 antigen. Thus, antibodies to the K88 adherence factor; the K88 pilus, will protect. Other adhesin type antigens designated, K99 987P, F41 have also been identified as important in piglet enteric colibacillosis. These, like the K88 adhesin could be used in the construction of a vaccine as demonstrated here fore K88 pilus antigen.

We have used *Salmonella typhimurium* strain G30 (a galE mutant) as the carrier strain.

Plasmid pFM 205 which encodes the cloned K88 antigen from enterotoxigenic *E. coli* has been introduced into strain G30. Mice were then immunized by feeding $10^8$ live bacteria or injecting intraperitoneally $5 \times 10^7$ formalin killed bacteria. Immunization was performed 3 times at weekly intervals. After one month the mice were bled and then sacrificed and their intestines removed and washed. The levels of antibodies to K88 were determined by ELISA using purified antigen (homogeneous by polyacrylamide gel electrophoresis). The results show (Table 2) that oral immunization produced a level of serum antibodies similar to that produced by intraperitoneal immunization. In contrast no detectable antibodies were produced in the gut when the bacteria were injected intraperitoneally whereas good gut antibody levels were induced as a result of oral immunization.

TABLE 2

Antibody production against purified K88 pili

| Immunization | ELISA Titre | |
|---|---|---|
| | Serum | Gut washings |
| G30 orally | <256 | <256 |
| G30 intraperitoneally | <256 | <256 |
| G30/pFM205 orally | 32768 | 4096 |
| G30/pFM205 intraperitoneally | 131071 | <256 |
| Normal mouse serum | <256 | |

EXAMPLE 2

A live bacterial strain effective for protection against a neonatal diarrhoea due to enterotoxigenic K99 *E. coli* for calves, lambs and piglets.

The introduction of a plasmid harbouring the K99 pilus, pRI9906-1 for example, into strain G30 is also another useful vaccine according to this invention. Such a vaccine would protect calves, lambs and piglets against neonatal diarrhoea due to enterotoxigenic K99 *E. coli*.

EXAMPLE 3

The introduction of plasmids harbouring the colonization factor antigens (CFA) of enterotoxigenic *E. coli* pathogenic for man would be further examples according to this invention. Such vaccines would protect against traveller's diarrhoea produced by enterotoxigenic *E. coli* of the homologous type.

Figure 20:
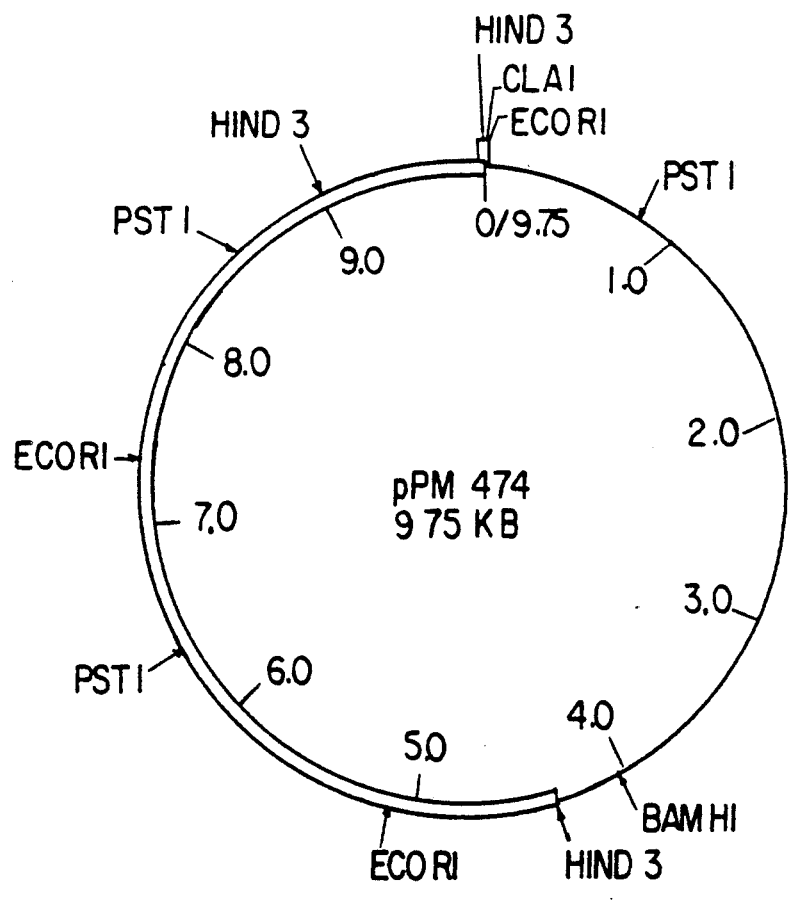
FIG. 20: Restriction map of plasmid pPM474. The thick line corresponds to the region of the CFA/II plasmid which has been cloned.

Several known colonization factors have been described in enterotoxigenic *E. coli*: CFA/I, CFA/II, CFA/III and E8775. These antigens each represent a single fimbrial type with the exception of CFA/II where three possible surface antigens may be produced depending upon the biotype of the strain. These three designated CS1, CS2 and CS3, CS1 and CS3 are expressed in strains of the A biotype and CS2 and CS3 in the biotypes B, D and F. The genes for CS3 have been cloned in a series of plasmids of which pPM474 has been analyzed in detail and represents the type (FIG. 20). Contiguous DNA has also been cloned as in plasmids pPM476, pPM477 and pPM483 and these are thought to encode at least CS1 and possibly CS2 in addition to CS3.

Figure 21:
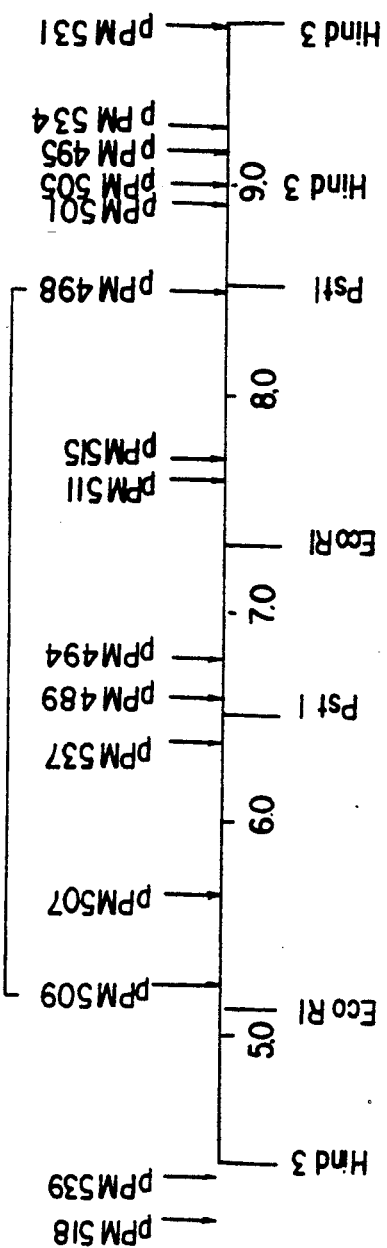
FIG. 21: Sites for insertion of transposon Tn1725 into the cloned CFA/II DNA present in pPM474. The co-ordinates are the same as in FIG. 20. Those transposon insertions which have been bracketed have lost the ability to produce CS3.
Figure 22:
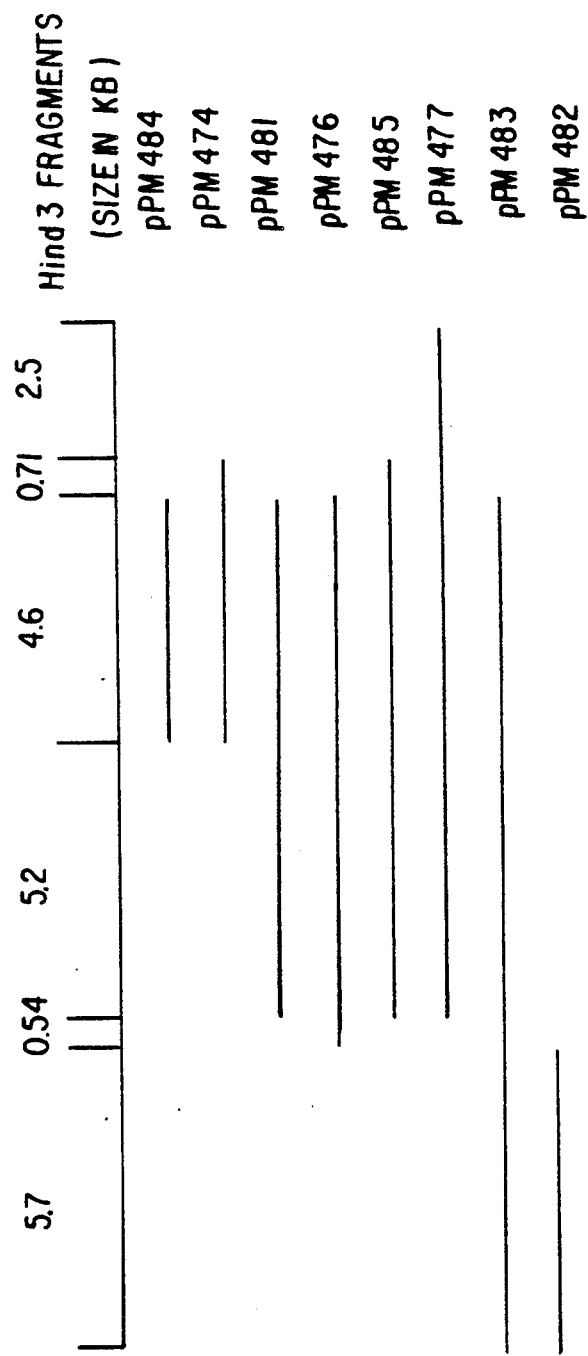
FIG. 22: Map of the contiguous HindIII fragments of the CFA/II plasmid which have been cloned into the HindIII site of the plasmid vector pBR322 to give the plasmid derivatives shown.
Figure 23:
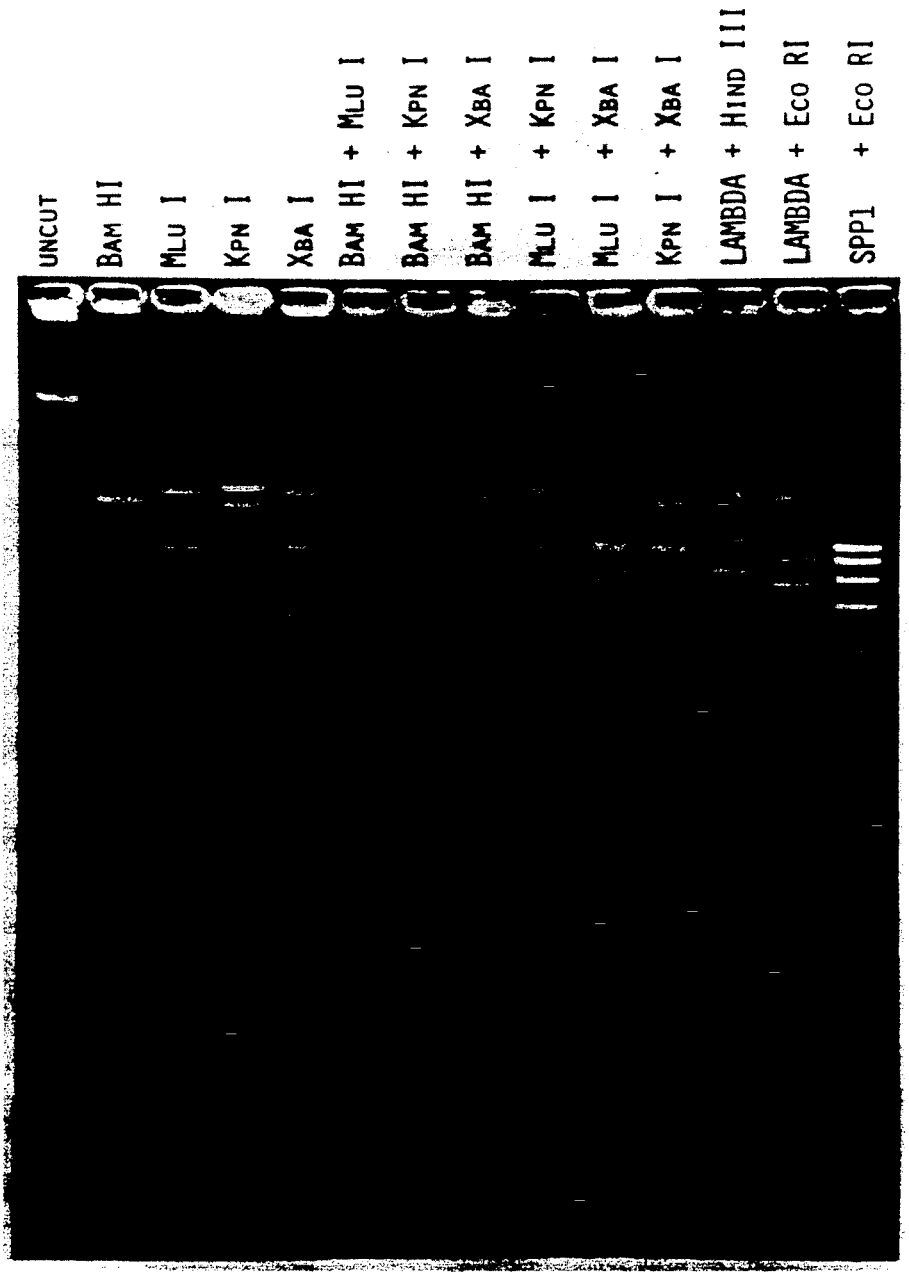
FIG. 23: Restriction endonuclease analysis of the DNA of plasmid pPM1001.
Figure 24:
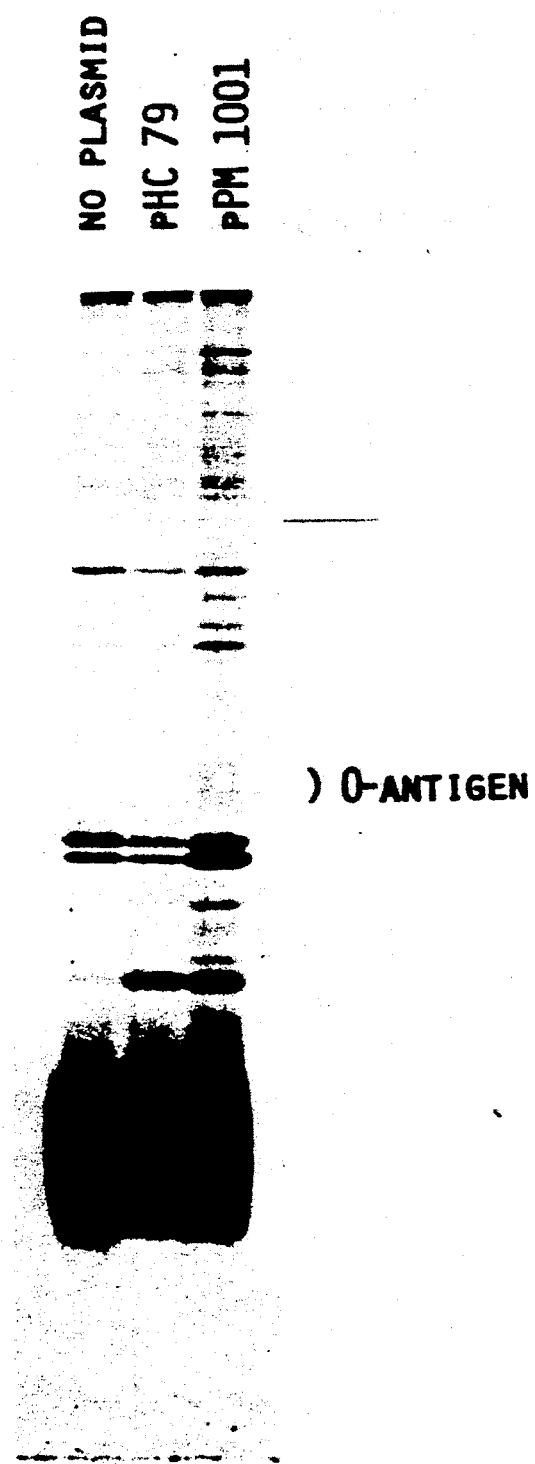
FIG. 24: Cell envelopes of *E. coli* K-12 strain DH1 containing the appropriate plasmids. Cell envelopes were analyzed by SDS-polyacrylamide gel electrophoresis followed by silver staining to visualize the bands.

Transposon insertion analysis of pPM474 has shown that a region of at least 3.5 kb is responsible for CS3 production (FIG. 21). This implies that it is a genetically complex process since the amount of DNA required to encode a protein the size of the subunit is only about 500 base pairs. Evidence that plasmids containing contiguous DNA encode at least CS1 in addition, comes from the fact that a spontaneous deletion of the wild type CFA/II plasmid which has lost the ability CS1 and CS3 had deleted about 15 kb. The end of the deletion corresponds to the 0.71 kb fragment on the right end of our cloned DNA. Thus both CS1 and CS3 are encoded within 15 kb to the left, and we have cloned about 16 kb (see FIG. 20).

An example of a particular useful vaccine according to this invention is the introduction of plasmid pPM474 harbouring the CS3 antigen of CFA/II into *S. typhi* strain Ty21a.

EXAMPLE 4

This now describes a useful bacterial strain useful as an oral vaccine against *Vibrio cholerae*.

The currently available parenteral killed vaccine against cholera is virtually useless. Firstly, the bacteria have been killed which is likely to damage or destroy a variety of surface antigens which may be very important. Secondly, the route of immunization is not appropriate for the generation of antibodies of the IgA class on the mucosa of the gut. Thus, we have set about developing a superior live vaccine harbouring the antigens of importance and which can get to the optimal site of mucosal antibody (Iga) stimulation, the Peyer's patches.

The vaccine, a further example of this invention, is a live bivalent oral vaccine, being simultaneously protective against *Salmonella typhi* and *Vibrio cholerae*. The vaccine is based on a galactose epimeraseless (galE) derivative of the *Salmonella typhi* strain Ty2. Such a mutant *S. typhi*, namely Ty21a, has been shown to be a safe live oral vaccine capable of inducing protection against typhoid fever. Its preparation and properties are described in U.S. Pat. No. 3,856,935 to R. Germanier. This aspect of the invention involves the cloning, by recombinant DNA or genetic engineering techniqus, of surface antigens of *Vibrio cholerae* and the introduction of these antigens into a *S. typhi* galE strain to produce a genetic hybrid. The hybrid is essentially the *S. typhi* galE strain containing and expressing the DNA for specific antigens of *Vibrio cholerae*.

The surface antigens of *Vibrio cholerae* upon which this vaccine is based fall into two classes, either the lipopolysaccharide (LPS) or surface proteins. These antigens are referred to as protective or target antigens in that they can induce the production of antibodies which will protect against Vibrio cholerae.

Cloning of the Protective Antigens

Vibrio cholerae strains 569B (a Classical Inaba strain) and 017 (an E1 Tor Ogawa strain) have been used as the source of donor chromosomal DNA for the various cloning experiments. This DNA was partially digested with one of the restriction endonucleases Sau3A, BamH1 or Pst1.

The vector DNA, pBR322, was digested with BamH1 (for cloning either Sau3A or BamH1 digested chromosomal DNA) or Pst1 and subsequently treated with alkaline phosphatase to prevent self-ligation. The two DNAs were mixed, ligated overnight, and transformed into a restrictionless *E. coli* K12 strain. Transformants were selected on nutrient media containing either amplicillin (when using BamH1 digested pBR322) or tetracycline (when pBR322 has been digested with Pst1). Such experiments resulted in greater than 80% of the transformants containing chromosomal inserts in the vector.

The transformants were patched onto numbered grids on nutrient medium containing the appropriate antibiotic and grown up overnight at 37°. They were then transferred to nitrocellulose discs for processing by colony blotting. This involved lysing the colonies on the filter with 0.5N HCl followed by removal of the unbound cell debris using a jet of water. The protein binding capacity of the filter was then saturated using bovine serum albumin, after which the primary antibody was added.

This antibody had been raised in rabbits against whole live 569B bacteria and the rabbits had been boosted with a crude preparation of adhesion material. Unbound antibody was then washed away and the secondary antibody added. This antibody was a conjugate of goat-antirabbit antibody and horse radish peroxidase. After washing to remove unbound conjugate the enzyme substrate was added to visualize those colonies expressing *Vibrio cholerae* antigens which could react with the primary antibody. Positive colonies isolated in this way were purified, rechecked in a colony blot and the cloned DNA/vector isolated and used to retransform *E. coli* K12 to confirm that the positive reaction was a plasmid property.

Plasmid pPM440 (and pPM450 and pPM460)

The invention could reside in one of the plasmids pPM440, pPM450 and pPM460. These plasmids were cloned independently using *Vibrio cholerae* strain 017 as the source of donor DNA. The three plasmids are apparently identical and we have used pPM440 for further characterization. This plasmid contains an insert of about 2.2 kb and a restriction endonuclease cleavage map is shown in FIG. 1. The term kb is used herein to DNA length and refers to the number of kilo-base pairs.

Figure 2:
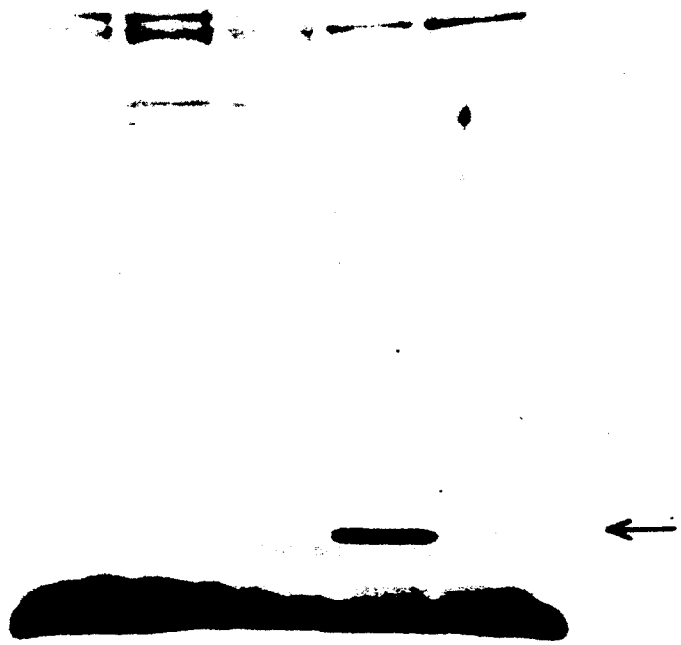
FIG. 2: Western blot analysis of cell envelopes of *E. coli* K-12 strains harbouring the various plasmids and using antisera against live *Vibrio cholerae* 569B.

In order to identify the gene products which we had cloned and which were reacting with the antiserum in the colony blotting, cell envelopes were prepared. The envelopes were solubilized in SDS and run on an SDS-polyacrylamide gel. The material in the gel was then electrophoretically transferred to nitrocellulose which was in turn treated similarly to the procedure used for colony blotting. The result of such a transfer is shown in FIG. 2. This clearly shows the presence of a band of about 22000 daltons present in pPM440 and not in either the vector or negatively reacting clones. This protein can also be seen in the cell envelopes after SDS-polyacrylamide gel electrophoresis (SDS-PAGE) followed by protein staining.

Two deletion derivatives of pPM440 have been constructed. The first of these, pPM441, was made by deleting from the HindIII site in the vector DNA clockwise to the HindIII site in the cloned DNA (see FIG. 1). The second deletion, pPM442, was obtained by deleting the DNA between the HpaI sites in the cloned DNA. Both of these deletions removed the ability to react with antiserum.

A series of transposon Tn1725 insertion derivatives of pPM440 have been isolated: pPM443–pPM448. Of these, strains harbouring pPM447 and pPM448 both give a positive colony blot although pPM447 is weaker than pPM448 and the parent plasmid pPM440. The other plasmids do not react at all.

Figure 3:
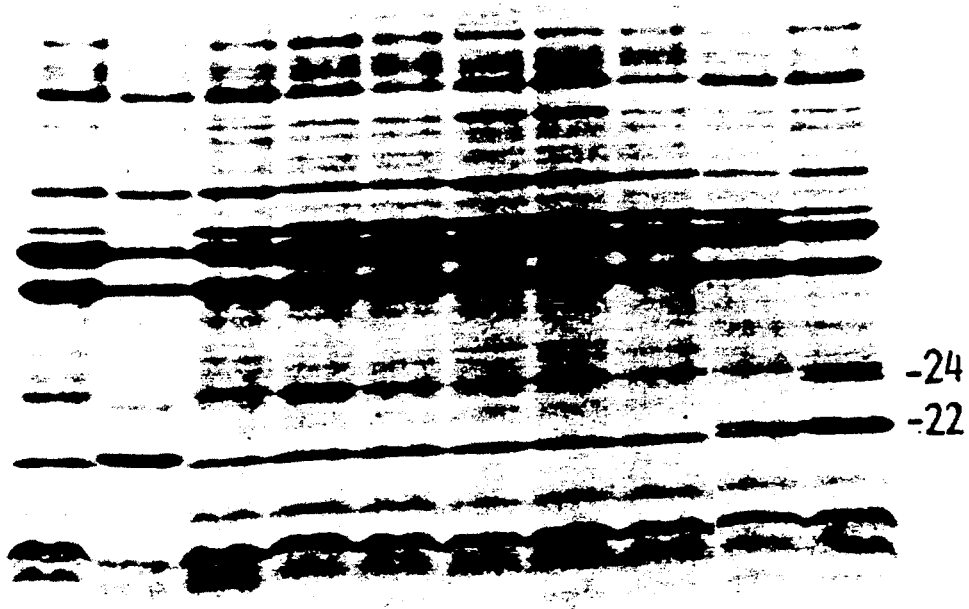
FIG. 3: analysis by SDS-PAGE followed by staining, of cell envelopes of *E. coli* K-12 harbouring the various plasmids.

If one examines by SDS-PAGE the cell envelopes of strains harbouring these plasmids, both deletion and insertion, then pPM448 produces normal levels of the 22000 dalton protein, compared to pPM440, whereas pPM447 has reduced levels and all the others have no detectable protein (FIG. 3).

Figure 4:
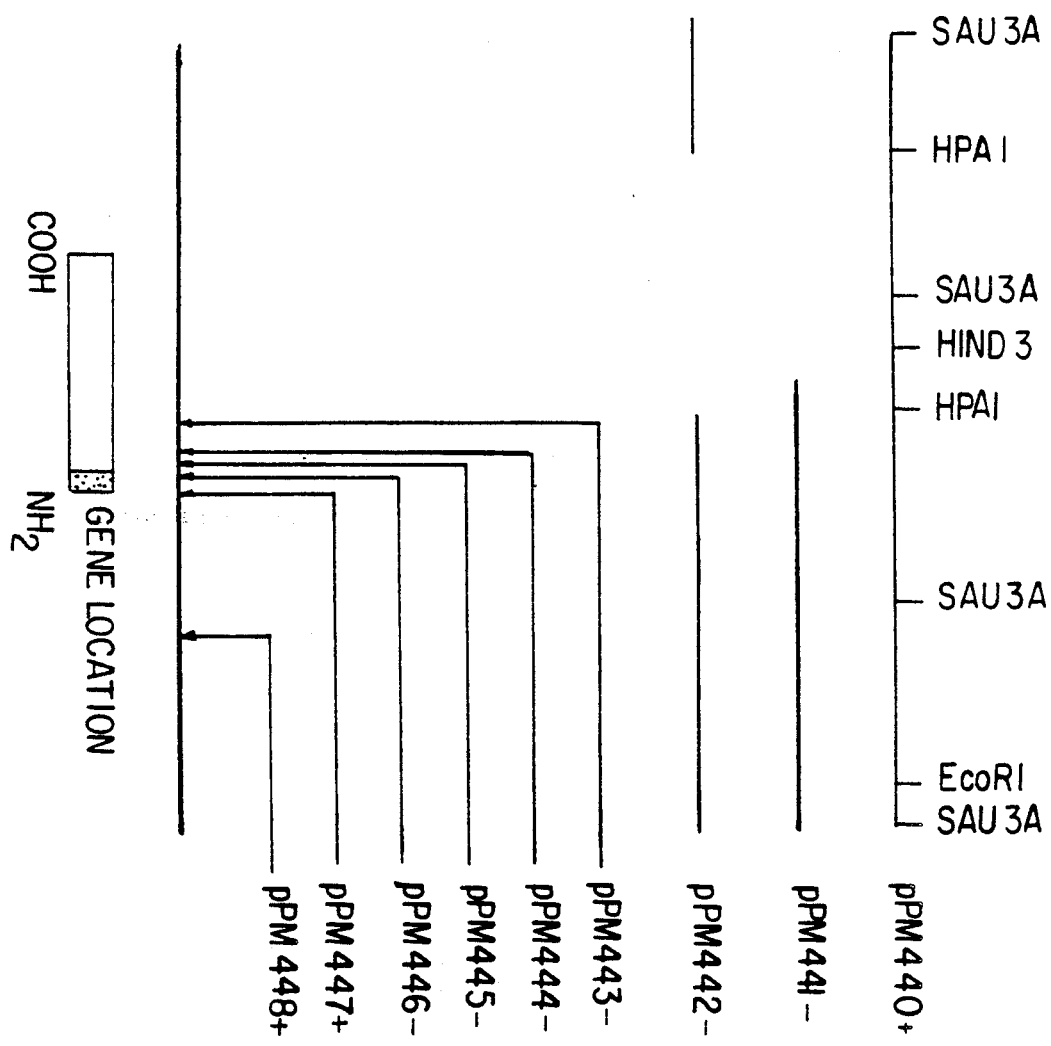
FIG. 4: Physical mapping of the gene for the 22000 dalton protein of pPM440 with respect to the deletions, pPM441 and pPM442, and transposon Tn1725 insertions, pPM443-pPM448.

In FIG. 4 a composite of all the restriction analyses of these various plasmids is shown. Using these data and the observation that the Tn1725 insertion in pPM447 is probably a polar insertion leading to lowered levels of the 22000 dalton protein, the position of the DNA encoding the 22000 dalton protein can be mapped as shown at the bottom of FIG. 3. The $NH_2$-terminus of the protein is probably encoded at the right hand end.

Figure 5:
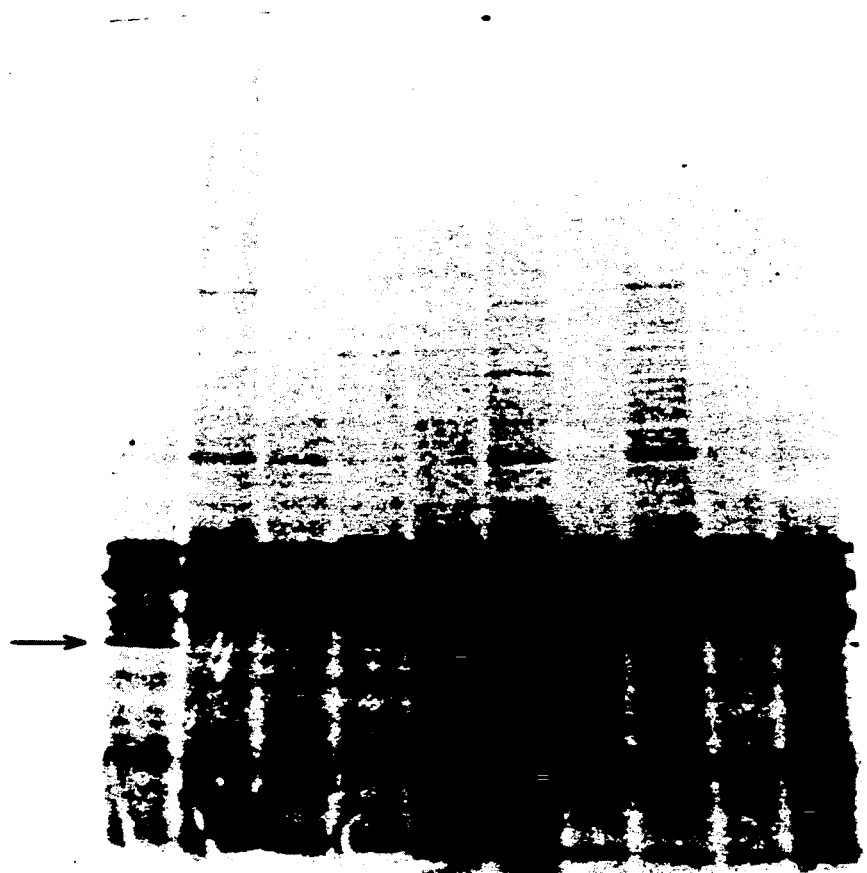
FIG. 5: Analysis of the plasmid encoded proteins in minicells harbouring the various plasmids by labelling with ($^{35}$S)-methionine, followed by SDS-PAGE and autoradiography.

If one examines the proteins encoded by all of these plasmids in minicells then the same result is obtained (FIG. 5). These results also show that the only new protein detected in pPM440 as compared to the vector, pBR322, is the 22000 dalton protein and that this protein is coded for on the plasmid.

Southern Blotting Analysis

Using the technique of DNA/DNA hybridization according to Sourthern we have used pPM440 as a probe to look at the similarity of this region of the chromosome in different *Vibrio cholerae* strains. Analyses using three different restriction enzymes demonstrated that the DNA cloned in pPM440 is present in both Classical and E1 Tor strains, and no discernible difference could be detected between strains. This implies that the gene and protein are common to both Biotypes of *Vibrio cholerae*.

Characterization of the pPM440 Protein

Figure 6:
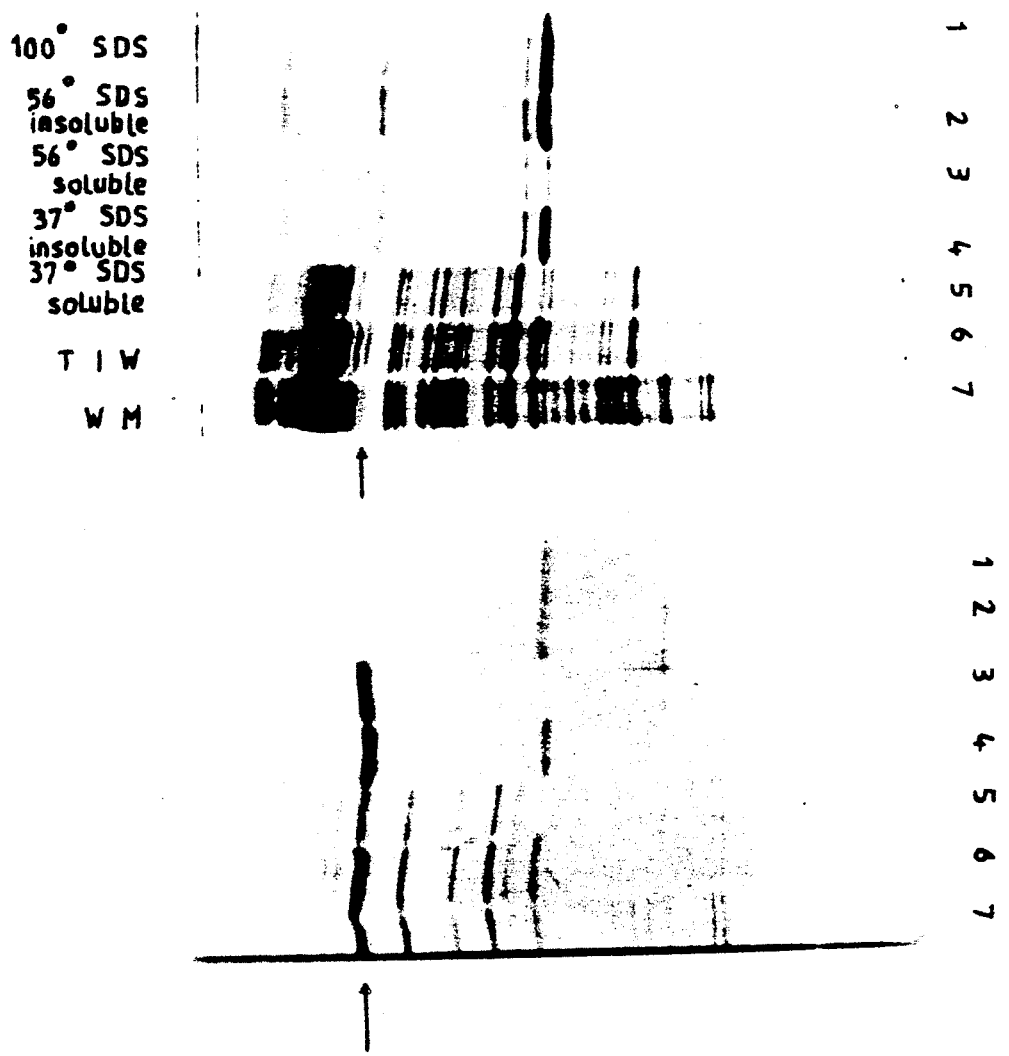
FIG. 6: Characterization of the 22000 dalton pPM440 protein by differential extractions following by SDS-PAGE and staining (left panel) or Western blot analysis with anti-live-*V. cholerae* 569B serum (right panel).
Figure 7:
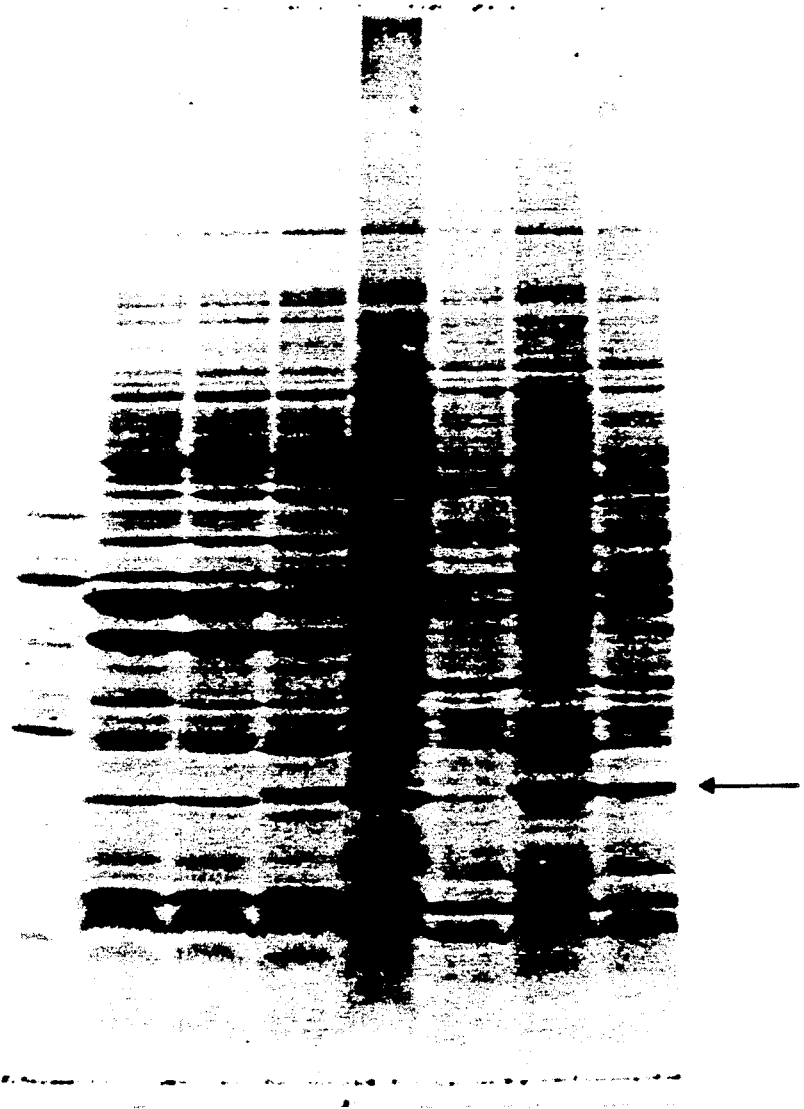
FIG. 7: Analysis by SDS-PAGE followed by staining of cell envelopes of the various strains harbouring the plasmids. The arrow indicates the cloned *Vibrio cholerae* surface antigen, the 22000 dalton protein.
Figure 8:
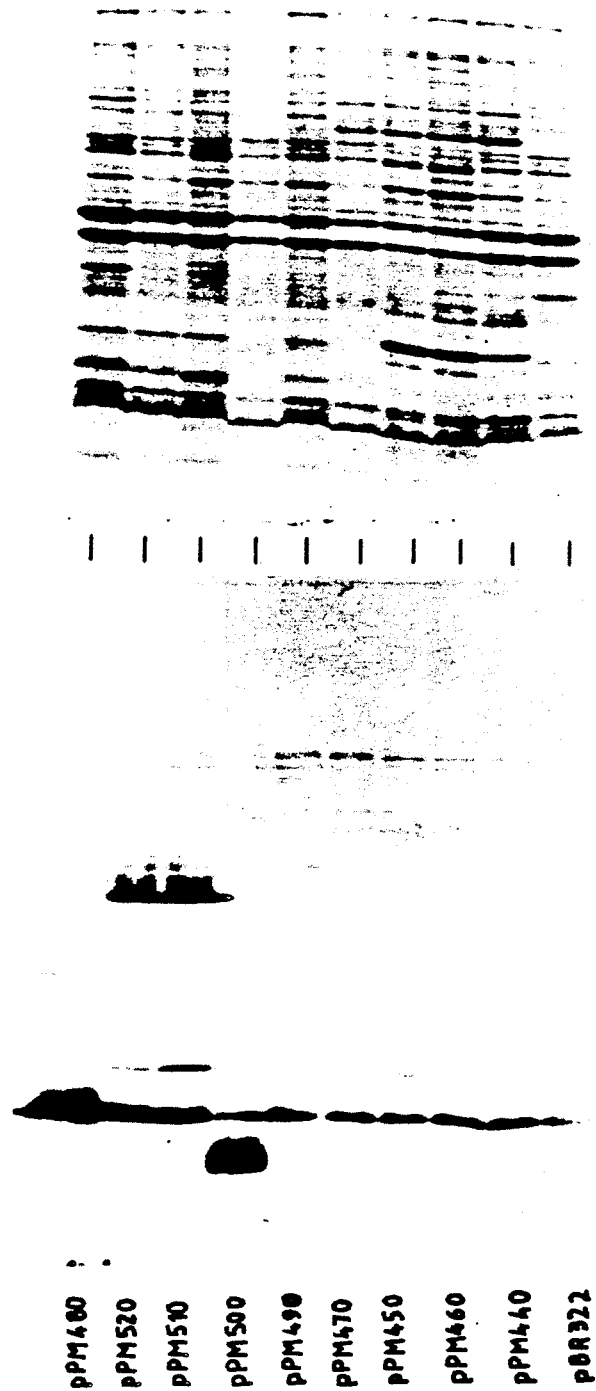
FIG. 8: Western blot analysis of *E. coli* K-12 derivatives harbouring the various plasmids. Cell envelopes of these strains were isolated and analyzed on SDS polyacrylamide gels followed by either staining with Coomassie blue (upper panel) or by Western blot analysis using anti-live-569B serum after the proteins had been transferred to nitrocellulose (lower panel).
Figure 9:
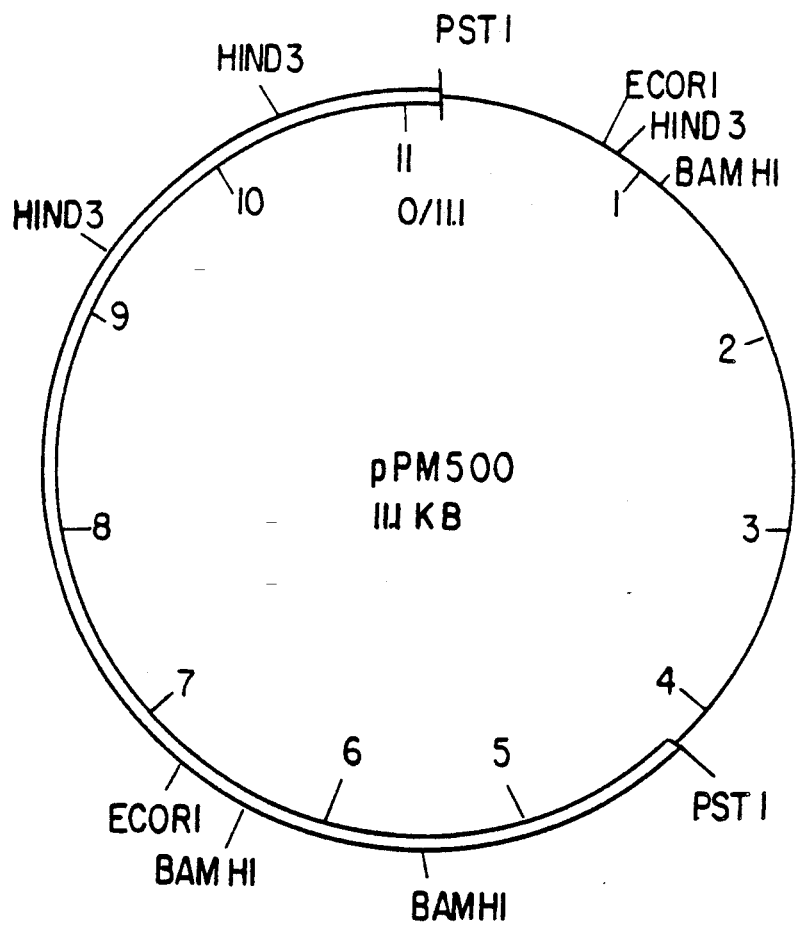
FIG. 9: Restriction map of plasmid pPM500. The thick line represents the region of cloned *V. cholerae* DNA.
Figure 10:
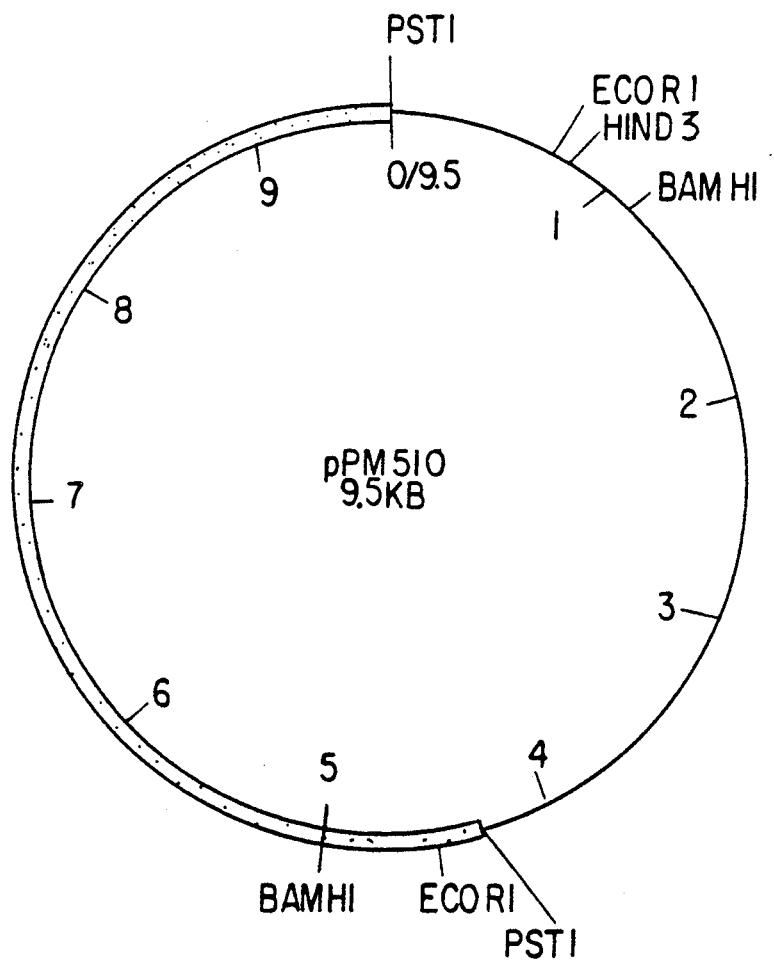
FIG. 10: Restriction map of plasmid pPM510. The thick line indicates the region of cloned *V. cholerae* DNA.
Figure 11:
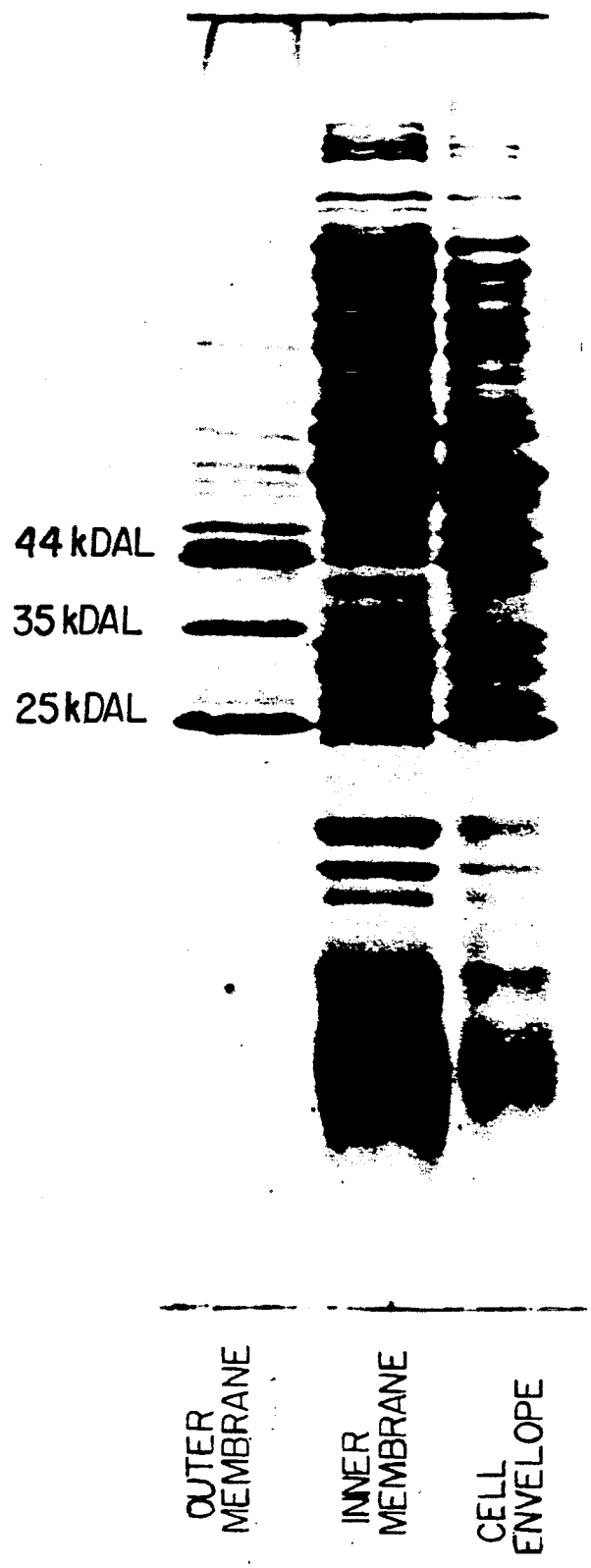
FIG. 11: SDS polyacrylamide gel electrophoresis of whole cell envelopes of *V. cholerae* and inner and outer membranes obtained by separation on sucrose density gradients.
Figure 12:
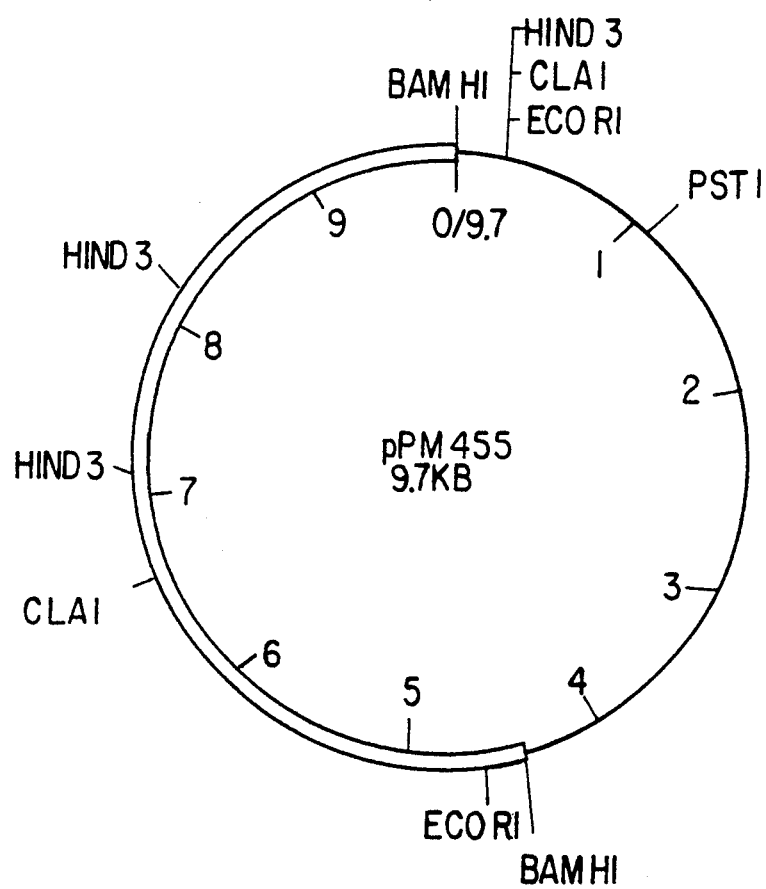
FIG. 12: Restriction map of plasmid pPM455. The thick line corresponds to the region of cloned *V. cholerae* DNA.
Figure 13:
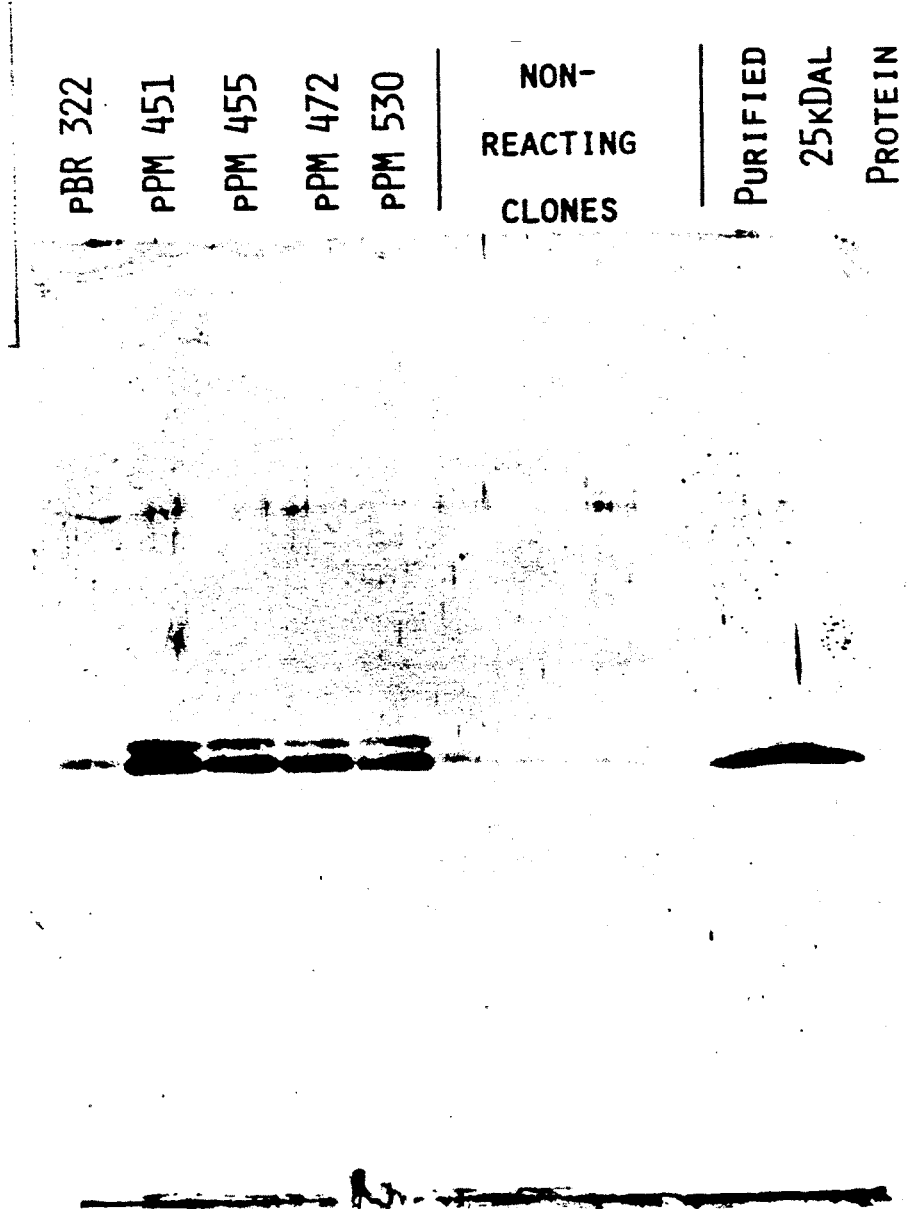
FIG. 13: Western blot analysis using anti-25 kDal protein serum with the cell envelopes of *E. coli* K-12 harbouring the various plasmids. Purified 25 kDal protein (OmpV) is shown for comparison.
Figure 14:
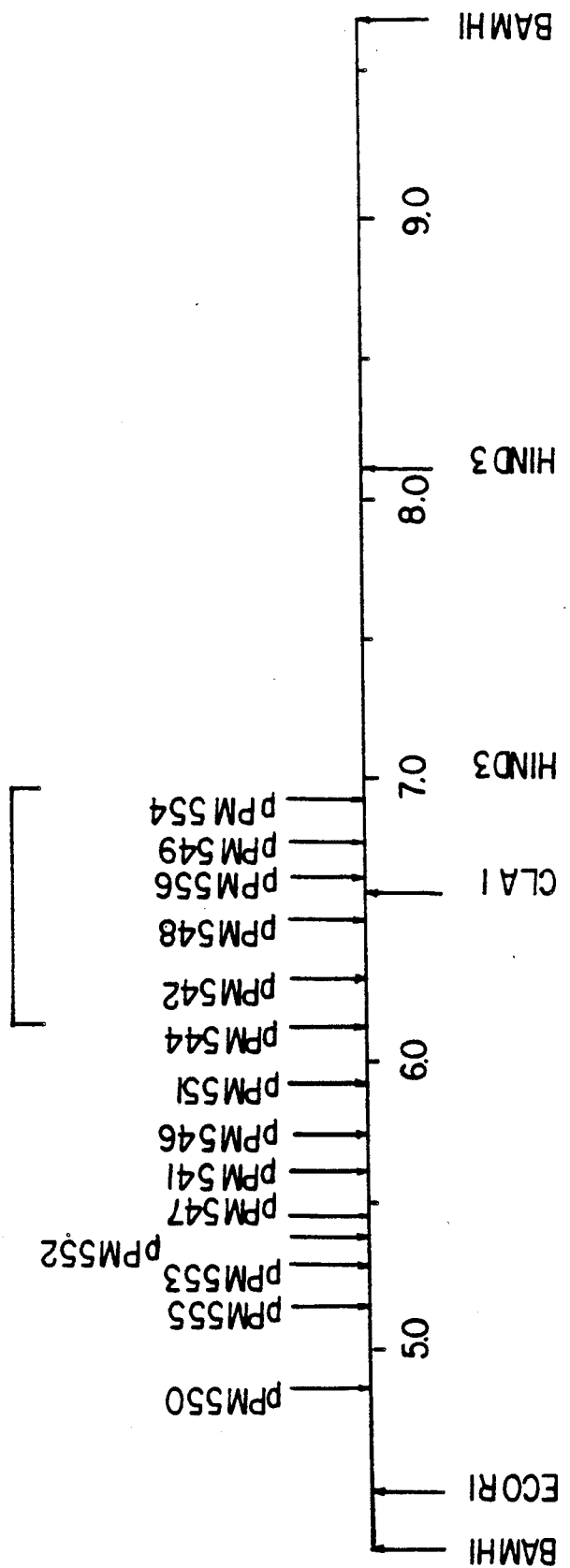
FIG. 14: Mapping of points of insertion of transposon Tn1725 in the various plasmid derivatives of pPM455, the transposon in plasmids pPM544, pPM542, pPM548, pPM556, pPM549 and pPM554. All eliminate the ability to detect the OmpV protein and lie within the gene.
Figure 15:
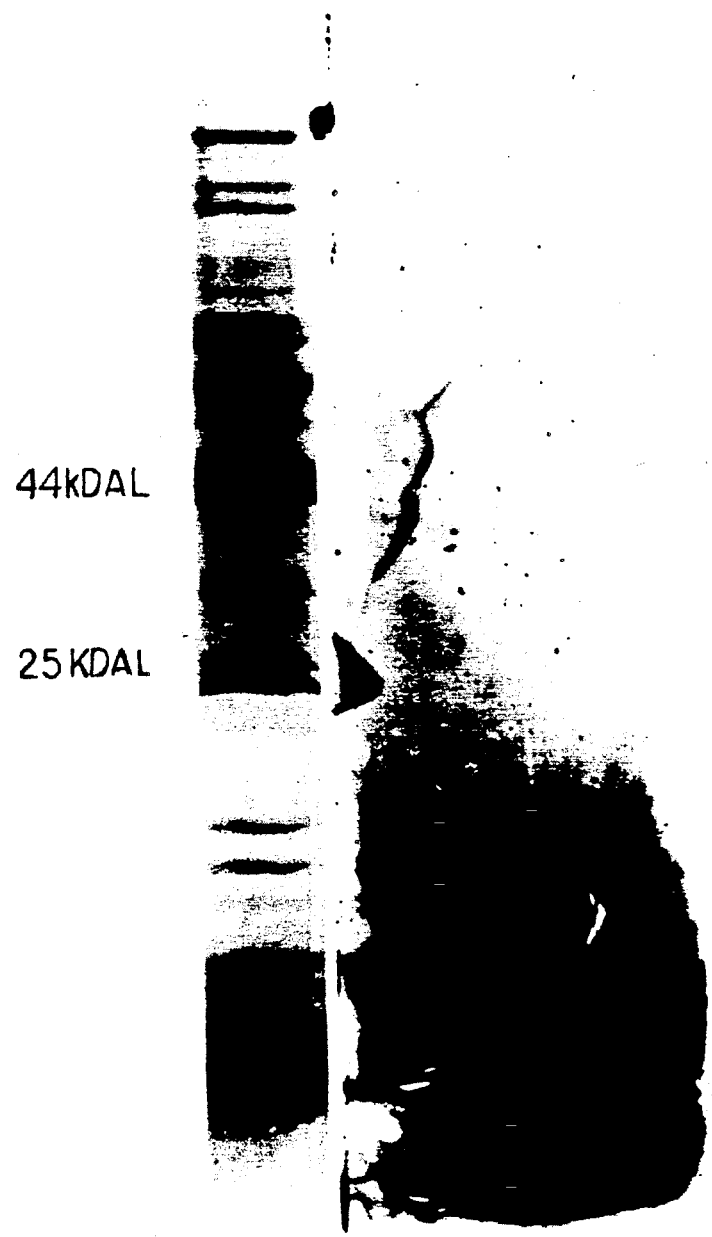
FIG. 15: Two dimensional crossed immuno electrophorsis of cell envelope proteins of *V. cholerae* strain 569B. Cell envelopes were run on SDS polyacrylamide gels in the first dimension, the strip cut out, equilibrated in Triton X-100 and electrophoresed into agarose containing antiserum to *V. cholerae* 569B.
Figure 16:
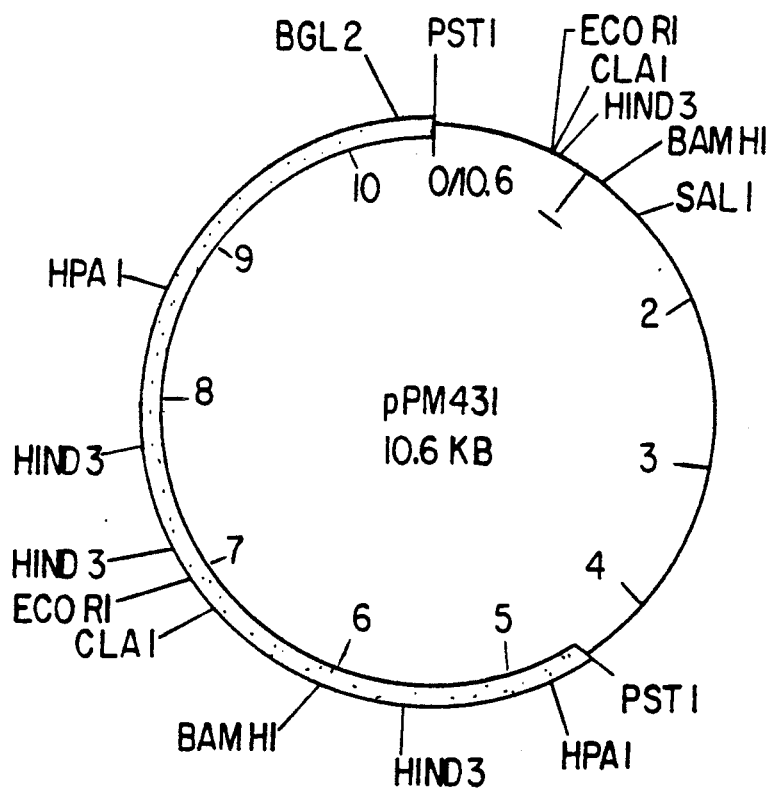
FIG. 16: Restriction map of plasmid pPM431. The thick line corresponds to the cloned *V. cholerae* DNA.
Figure 17:
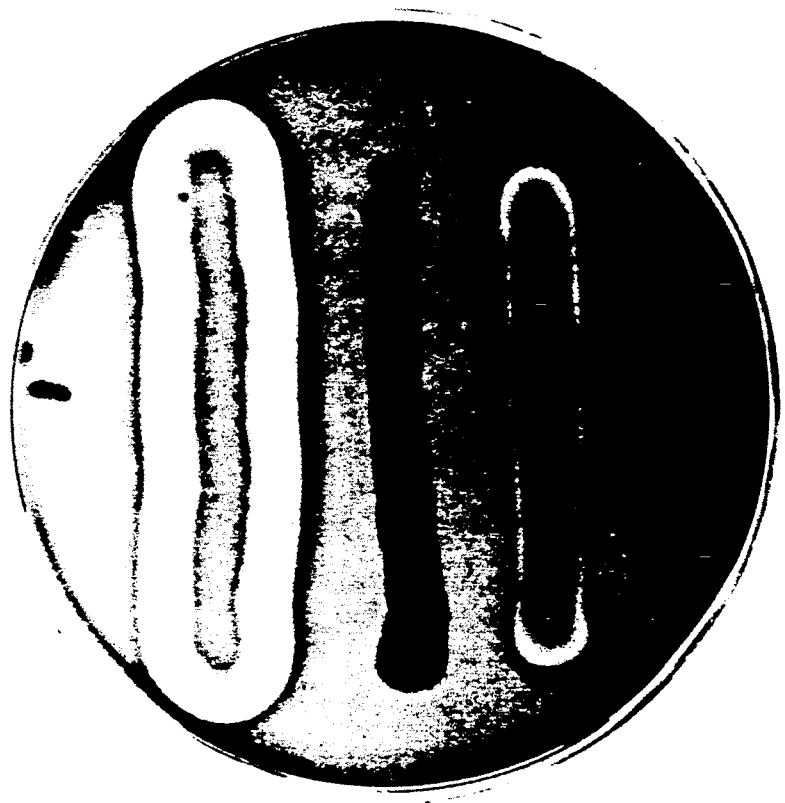
FIG. 17: Haemolysin production on nutrient agar containing 5% sheep red blood cells by *V. cholerae* strain 017 and *E. coli* K-12 strains harbouring the plasmids pBR322 (the cloning vector) and pPM431.
Figure 18:
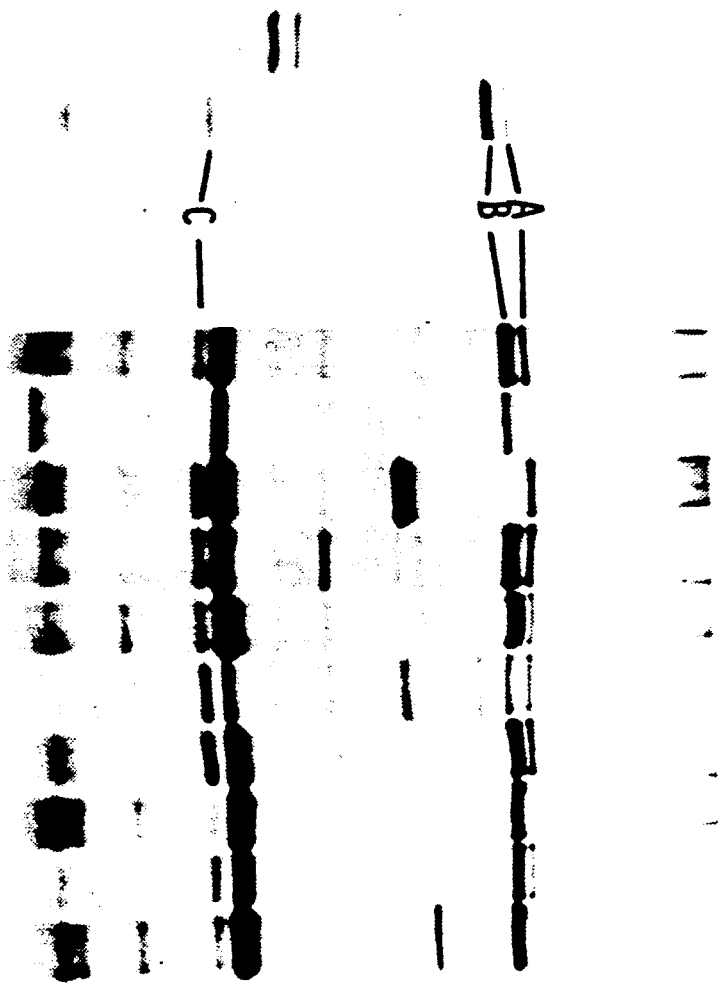
FIG. 18: Minicell analysis of transposon Tn1725 derivatives of pPM431. The plasmid encoded proteins were analyzed by labelling with ($35_s$) methionine followed by SDS-polyacrylamide gel electrophoresis and autoradiography.
Figure 19:
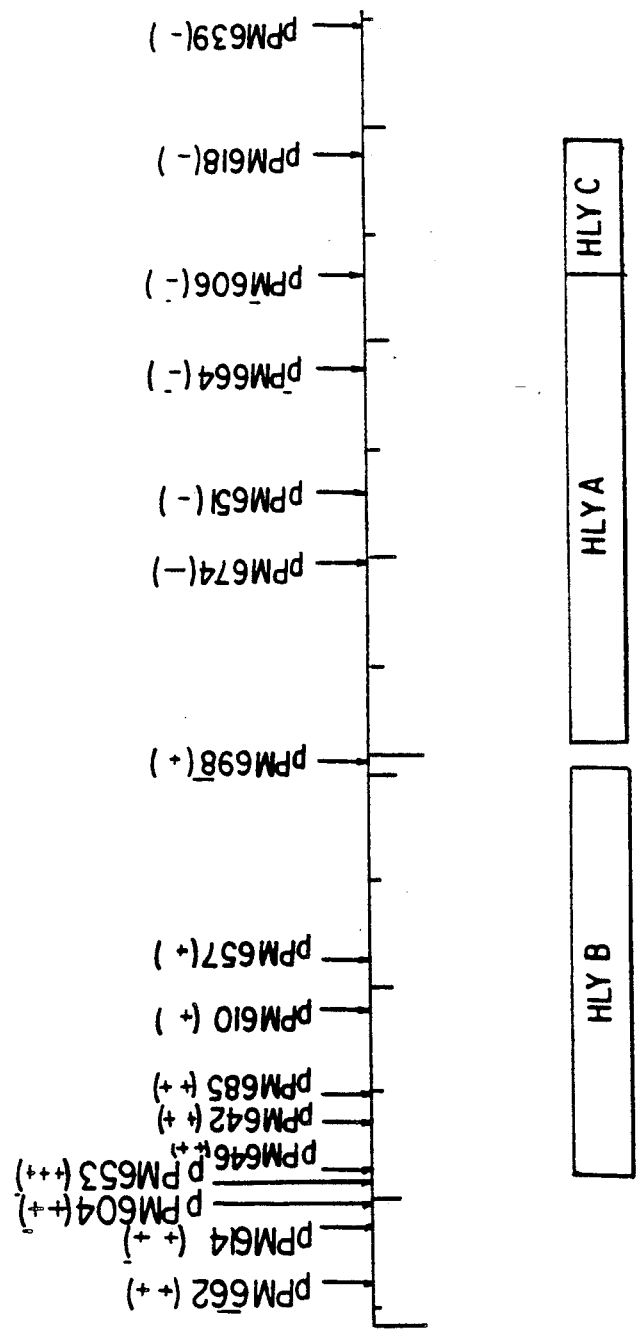
FIG. 19: Physical mapping of the *V. cholerae* DNA contained within pPM431. The points of insertion of Tn1725 in the various plasmids is shown as is the degree of haemolysis (−, +, ++, +++) compared to pPM431 (+++). The boxes represent the amount and location of DNA encoding each of the proteins.

The 22000 dalton protein encoded by pPM440 has been partially characterized and purified. In FIG. 6 are shown the results of SDS-PAGE after fractionating the cell envelope of cells of *E. coli* K12 harbouring the plasmid pPM440. The left panel shows the results obtained by staining the gel and the right panel shows a duplicate gel which has been analysed by a Western blot using *Vibrio cholerae* antiserum to identify the pPM440 protein. The results of the fractionation imply that the pPM440 protein is probably a peptidoglycan-associated outer membrane protein.

Fractionation of the protein in this way followed by ion-exchange chromatography on hydroxyapaptite in SDS followed by gel filtration on Biogel P150 in SDS has enabled the protein to be purified.

Expression of the pPM440 Protein in Salmonella

In order to carry out the relevant immunological testing and to determine whether or not the pPM440 protein is expressed in Salmonella, it was necessary to transform *S. typhimurium* strain G30 and *S. typhi* strain Ty21a with purified pPM440 plasmid DNA. The plasmid vector was also introduced as a control. Cell envelopes of these strains, *Vibrio cholerae* 569B and the original *E. coli* isolates were prepared and analysed by SDS-PAGE. The results are shown in FIG. 7. It can be seen that the pPM440 protein is only a minor protein in *Vibrio cholerae*, not being readily detected. However, in the cloned form in *E. coli, S. typhimurium* and *S. typhi* the protein is a major band.

All of these strains have been analysed for their ability to be aggulutinated by *Vibrio cholerae* 569B antiserum. The results of these agglutinations are shown in Table 3. In these tests it was observed that when pPM440, and thus the 22000 dalton protein, was present the cells showed significant autoagglutination. This is suggestive of the 22000 dalton protein being an adherence factor. The data show that antibodies to vibrio cholerae can agglutinate the strains harbouring pPM440. Thus not only is the protein being expressed in the Salmonella vaccine strains, but it is being expressed in a form which is recognizable by antibodies.

pPM440, therefore, appears to be useful in the form of an oral vaccine as described by this invention.

The invention could thus reside in immunizing an animal recipient (including man) by the steps of introducing into the animal by oral administration a pharmaceutically or physioligically acceptable carrier carrying therewith a *Salmonella typhi* galactose-epimeraseless (galE) mutant expressing the *Vibrio cholerae* surface antigen which we have cloned in the plasmid pPM440.

The invention could reside in the surface antigen being encoded on a plasmid.

The invention could reside in the surface antigen being chromosomally encoded, having been genetically engineered into the *Salmonella typhi* chromosome.

TABLE 3

AGGLUTINATION BY ANTISERUM TO LIVE VIBRIO CHOLERAE 569B

| Strain | | Titre+ |
|---|---|---|
| *V. cholerae* 569B | | 1000 |
| *E. coli* K12 | | <50 |
| | +pBR322 | <50 |
| | +pPM440 | 500* |
| *S. typhimurium* G30 | +pBR322 | <50 |
| *S. typhimurium* G30 | +pPM440 | 500* |
| *S. typhi* Ty21A | +pBR332 | <50 |
| | +pPM440 | 1000* |

+Titre is the reciprocal of the lowest dilution giving agglutination.
*Significant Autoagglutination Plasmid pPM500

A further example of this type could be the protein encoded by the plasmid pPM500. This protein is about 16–18 kDaltons in size and reacts very readily with antisera in a Western blot (FIG. 8).

Plasmid pPM500 consists of a 6.7 kb Pstl fragment of *V. cholerae* DNA cloned into the Pstl site of pBR322. The gene for the pPM500 protein has been localized by transposon mutagenesis and corresponds to a region of 400–500 base pairs spanning the HindIII site at 10.4 kb on the pPM500 map (FIG. 9).

Minicell analysis to detect the plasmid encoded proteins suggest that the pPM500 protein lacks methionine.

Plasmid pPM510 (and pPM520)

A further example of this type could be the plasmid pPM510 (FIG. 10) which encodes two proteins. These proteins are about 22 kDal and 60–65 kDal in size and both react strongly in a Western blot (FIG. 8).

Plasmid pPM510 consists of a 5.1 kb Pstl fragment cloned into the Pstl site of pBR322. The location of the genes for the proteins within the cloned DNA has not yet been determined but together they would take up about 50% of the coding capacity of the cloned fragment.

Plasmid pPM 451 (and pPM 455, pPM 472, pPM 530)

A further example of this type could be the 25 kDal OmpV protein, a major outer membrane protein of *V. cholerae* (FIG. 11), encoded on each of one of the plasmids pPM451, pPM455, pPM472 and pPM530. Detailed analysis has been performed using pPM455 and a restriction map of this plasmid is shown in FIG. 12. The 25 kDal protein has been identified by Western blot analysis (FIG. 13) and the location of the gene within the cloned DNA has been determined by deletion and transposon insertion analyses (FIG. 14). These analyses show that the OmpV gene lies between the point of insertion of Tn1725 in plasmid pPM551 and the HindIII site at 7.0 kb. Other studies involving generating fusion proteins in part derived from OmpV show that transcription is from left to right.

The OmpV protein appears to be very immunogenic (FIG. 15) and besides being a major outer membrane protein it is part of the sheath of the flagellum. Thus antibodies to this protein should immobilize the bacterium by binding to the flagellum, and in so doing prevent the *V. cholerae* from colonizing the gut.

Plasmid pPM431

A further example of this type which could be used in combination with others to increase protection is encoded by plasmid pPM431 (FIG. 16). This plasmid encodes several of the proteins associated with haemolysin production (FIG. 17). The genes have been localized by transposon insertion analysis and by determining the plasmid encoded proteins in minicells (FIG. 18). These results have enabled a partial physical map of the plasmid to be determined (FIG. 19). Most importantly, HlyA the structural gene for the haemolysin is encoded within this DNA.

The importance of the haemolysin protein in protection is that it has been shown to be diarrhoeagenic in rabbit ileal loops. Thus, antibodies in the gut could be expected to be beneficial in reducing diarrhoea due to this excreted protein.

Deletion of the gene(s) determining haemolysin production or part thereof in attenuated *V. cholerae* strains may also be useful in generating vaccine strains different to the type described in this document. In particular, if haemolysin is responsible for some diarrhoea in cholera-toxin-less *V. cholerae* then deletion or inactivation would greatly improve those strains.

EXAMPLE 5

Very specific difficulties were experienced in relation to this example.

It was suspected that an O-antigen of *Vibrio cholerae* could be useful.

It was known that an antibody directed against *Vibrio cholerae* O-antigen could be very effective in protection against *Vibrio cholerae* in animal model systems and in man. It was also known that the O-antigen induces a good immune response and hence would be the ideal antigen for a vaccine strain of the above type.

It was known from work with respect to Salmonella that the genes which enable the synthesis of the O-antigen polysaccharide monomer are mostly present in one cluster of genes, located at about 42 minutes on the Salmonella genetic map. Some of these genes encode enzymes for synthesis of constituent monosaccharides and others encode enzymes for assembly of the monomer on a lipid carrier. It was guessed at that this gene cluster would occupy a substantial segment of DNA.

It was also known from work with respect to Salmonella that the genes which determine polymerisation of the O-antigen monomer to O-antigen polymer and the genes which encode the translocase which translocates the O-antigen polymer to the lipopolysaccharide (LPS) core to give the complete lipopolysaccharide molecule are both located away from the major gene cluster.

It was to be expected by comparison with Salmonella that the genetic basis for *Vibrio cholerae* O-antigen synthesis would be equally complex and further that even if the entire set of genes necessary for synthesis of *Vibrio cholerae* O-antigen were cloned and transferred to *E. coli* or Salmonella, that the O-antigen polymer may not be transferred to the *E. coli* or Salmonella lipopolysaccharide core which differs from the *Vibrio cholerae* LPS core.

The difficulties in cloning the O-antigen synthesis system such that it can be expressed on the LPS of *E. coli* or Salmonella are thus firstly that the major gene cluster may occupy a substantial length of DNA, secondly that there may be other genes essential for full expression not present in the main cluster and thirdly, that the genes even when cloned and placed together in *E. coli* or Salmonella may not fully express the O-antigen on the cell surface due to differences in the lipopolysaccharide cores of these organisms and *Vibrio cholerae*, such that the translocases would not transfer the *Vibrio cholerae* O-antigen polymer to the *E. coli* or Salmonella core.

Because of the anticipated enormous difficulties in cloning the full set of genes necessary for *Vibrio cholerae* O-antigen to be expressed on the surface of *E. coli* or Salmonella, we have been looking primarily for clones encoding surface proteins of *Vibrio cholerae* which may induce effective immunity when present in suitable vaccine strains of *Salmonella typhi* or a related organism. However, in addition, we conducted our experiments in such a way that should a set of genes be cloned which enabled the O-antigen of *Vibrio cholerae* to be expressed on the surface of *E. coli*, then that would be detected by our screening method.

In our first attempts at cloning, we used the cosmid vector pHC79 as such a vector should enable the cloning of clusters of genes on DNA of the order of 30–40 kb in size. However, the *Vibrio cholerae* DNA obtained by the conventional methods was of low molecular weight, presumably due to partial degradation by the extracellular DNAase produced by *Vibrio cholerae*. We therefore had to proceed with cloning into plasmid vectors and obtained many clones which expressed *Vibrio cholerae* surface proteins in *E. coli*, but all contained only small pieces of *Vibrio cholerae* DNA, averaging from 2 kb to 8 kb depending on the restriction enzyme used. We then devised a method for extracting *Vibrio cholerae* DNA in the presence of pronase, such that it remained in a high molecular weight form which could be then cut by restriction enzymes into pieces of 30 to 40 kb in size suitable for cloning into cosmids.

We have now discovered that indeed *Vibrio cholerae* carries genes which are within a common locality such that they can be cloned as a group into a cosmid and determined the synthesis of the *Vibrio cholerae* O-antigen in *E. coli*.

Furthermore, it has been discovered that the DNA length effective for this purpose is large but less than 40 kb.

Furthermore, we have discovered that there is indeed a technique which when used with respect to such material as *Vibrio cholerae* chromosomal DNA can keep this material in sufficiently high molecular weight pieces while at the same time providing sufficient concentration and purity of such material that this can be useful to obtain fragments in the 40 kb pair range and which are useful for subsequent cloning techniques.

We have discovered that if the cells are lysed in the presence of pronase and if separation and concentration is effected using solvent extraction where the chromosomal DNA is kept within the same container during this process, then the DNA strands can be isolated with very long lengths.

The integrity of the DNA is also assisted by the fact that the extraction process can be effected somewhat quicker than if centrifugation on Caesium chloride gradients is used and this reduces the time during which DNAase is kept in contact with the otherwise integral material.

The specific preferred technique for obtaining such extended lengths of DNA or further cloning techniques will be described in a later part of this specification.

Specifically however, having been able to obtain chromosomal DNA of large molecular weights from each of *Vibrio cholerae* strains 569B (a classical Inaba strain) and 017 (El Tor, Ogawa), this chromosomal DNA was then partially digested by using an appropriate restriction endonuclease which could be expected to leave at least some fragments in the range of approximately 35 through 50 kb pairs.

In preference, the restriction endonuclease Sau3A was used for this purpose and was indeed effective to provide appropriate restriction fragments.

Proceeding on the assumption that even a protein antigen suitable for vaccine purposes might be better expressed from a gene cluster capable of being contained within a DNA strand of approximately 40 kb pairs in length cloning into a cosmid vector was proceeded with. Accordingly, DNA of the cosmid vector, pHC79, was completely digested with BamHI and subsequently treated with alkaline phosphatase to prevent self ligation.

The restriction fragments from the *Vibrio cholerae* and the cosmid vector DNA were then mixed, ligated overnight, and packaged in vitro into bacteriophage λ. The phage lysate was then used to infect a restrictionless (hsdR), recombination deficient (recA) *Escherichia coli* K-12 strain. Cosmid containing cells were selected on nutrient media containing ampicillin. Greater than 90% of these colonies obtained comprised cells which were sensitive to tetracycline (as expected if DNA is cloned into the BamHI site of the vector) which could be assumed to carry cosmid pHC79 with cloned *Vibrio cholerae* DNA. Such cells contained thereby cosmid clones containing between 35 to 50 kb pairs of DNA.

The colonies were then tested with antibody to determine if any produced *Vibrio cholerae* antigens as a result of carrying cloned *Vibrio cholerae* DNA.

Accordingly, the cosmid clones as obtained were then patched onto numbered grids on nutrient medium containing ampicillin and grown up overnight at 37° C. They were then transferred to nitrocellulose discs for processing by colony blotting. This involved lysing the colonies on the filter with 0.5N HCl followed by removal of the unbound cell debris using a jet of water. The protein binding capacity of the filter was then saturated using skim milk powder after which the primary antibody was added.

This antiserum or antibody had been raised in rabbits against whole live 569B bacteria and the rabbits had been boosted with a crude preparation of adhesin material. Unbound antibody was then washed away and the secondary antibody added. This antibody was a conjugate of goat-anti-rabbit antibody and horse radish peroxidase. After washing to remove unbound conjugate the enzyme substrate was added to visualize those colonies expressing *Vibrio cholerae* antigens which could react with the primary antibody. Positive colonies isolated in this way were purified, rechecked in a colony blot and the cosmid DNA isolated and used to retransform *E. coli* K-12 to confirm that the positive reaction was associated with the cosmid DNA. The positively reacting colonies were then further analysed by repeating the colony blotting and using other antisera in place of the anti-live-569B serum, including the anti-live-569B serum described above after it had been extensively adsorbed with purified LPS from *Vibrio cholerae* 569B to remove antibodies reacting with the LPS.

Clones encoding genes for the synthesis of the LPS should be detected by their inability to react in a colony blot with this antiserum after it has been extensively adsorbed with purified LPS.

According to this method several clones were identified as containing genes effective for the synthesis of the O-antigen of the LPS.

Our invention accordingly could reside in restriction fragments of DNA containing less than 40 kb of DNA and containing in a common location such genes effective for the determination of the O-antigen.

The invention then could be said to reside in the combination of the genes effective for the synthesis of O-antigen with a cosmid vector to produce thereby a cosmid clone this being a clone of the size between 35 to 50 kb pairs of DNA.

pPM1001 is exemplary and accordingly our invention can reside in the cosmid pPM1001.

Subsequent analysis of this cosmid reveals that it contains approximately 36 kb pairs *Vibrio cholerae* DNA cloned into pHC79. A gel electropherogram of the said DNA restricted with several endonucleases is shown in FIG. 23.

The presence of this cosmid identified as pPM1001 in the bacterial cell renders it capable of producing the O-antigen of the LPS of the Inaba serotype.

This material can be detected in several ways.

If cell envelopes are isolated from the bacteria harbouring pPM1001, solubilized in SDS and analysed by polyacrylamide gel electrophoresis followed by staining with silver then it is possible to detect the production of a ladder of bands typical of lipopolysaccharide containing O-antigen (FIG. 24). This same envelope material can also be electrophoresed in the same way, transferred electrophoretically to nitrocellulose and Western blotted using antiserum to the LPS. In this way, it is possible to detect the O-antigen material, by first reacting the nitrocellulose sheet with rabbit anti-*Vibrio cholerae* LPS serum, followed by goat-anti-rabbit serum to which has been coupled horse radish peroxidase and the immune complexes can be visualized by adding substrate for the peroxidase. Only the *V. cholerae* O-antigen is visualized in such a Western blot, and the positive reaction obtained showed that the LPS carried *Vibrio cholerae* O-antigen.

Purified LPS has also been extracted by the hot phenol-water method from *E. coli* K-12 harbouring either pHC79 or pPM1001. Upon electrophoresis followed by silver staining the presence of pPM1001 can be seen to lead to the ladder of bands typical of LPS carrying O-antigen (FIG. 25).

The purified LPS has also been used in a haemagglutination inhibition assay to see if it is capable of neutralizing anti-LPS immunoglobulin so as to prevent the agglutination of sheep red blood cells which have Inaba LPS fixed upon their surface. This assay demonstrated that the O-antigen material produced in *E. coli* K-12 as a result of harbouring pPM1001, was immunologically indistinguishable from the LPS of the Inaba parent *V. cholerae* strain 569B. LPS from the clone, Ogawa LPS or Inaba LPS, each in 2 fold serial dilutions, was used to inhibit either the agglutination by anti Ogawa serum of sheep red blood cells (rbc's) coated with Ogawa LPS or the agglutination by anti-Inaba serum of sheep rbc's coated with Inaba LPS.

In the Inaba coated rbc experiment, LPS from the clone inhibited to well 11 (1 μg/ml) compared to well 12 (0.5 μg/ml) for V. cholerae Inaba LPS. Ogawa LPS inhibited to well 7 (16 μg/ml). Thus LPS from the clone inhibits very well showing that it has all or most of the specificity of Inaba LPS.

In the Ogawa coated rbc experiment LPS from all three types inhibited to about well 15 (0.06 μg/ml). Thus the LPS from the clone inhibits to the same extent as *V. cholerae* Inaba LPS, showing that it carries the common antigenic specificities known to be shared by LPS from Inaba and Ogawa *V. cholerae* strains. LPS from *E. coli* carrying pHC79 gave virtually no inhibition in either system.

As already mentioned this LPS carrying O-antigen material being produced as a result of the cells harbouring pPM1001 is found in the cell envelope. It can further be shown to be exposed upon the cell surface since cells harbouring pPM1001 can be agglutinated by anti-LPS serum whereas cells harbouring no cosmid or corryin pHC79 cannot.

pPM1001 encodes the genes determining the Inaba serotype of V. cholerae. However, variation between the serotypes (Inaba and Ogawa) of *V. cholerae* has been localized to one locus and now that we have found that all the genes necessary for the expression in E. coli of Inaba O-antigen specificity can be cloned on one DNA fragment, it seems that through the invention the genes necessary for the expression in *E. coli* of Ogawa O-antigen can also nbe cloned on a single DNA fragment.

pPM1001 can be used to obtain a cosmid clone from a gene bank constructed using DNA from a vibrio cholerae (Ogawa) strain, such as 017: this could be done simply by using pPM1001 or part of the cloned vibrio cholerae DNA encoding O-antigen synthesis as a DNA probe to detect the Ogawa clone. Alternatively, the Ogawa genes could be cloned by the same procedure as used to isolate pPM1001 (except that an Ogawa antiserum must be used. In fact, we have succeeded in the isolation of the cloned Ogawa antigen by the same procedure. Plasmids pPM1002 and pPM1003 are exemplary and accordingly our invention could reside in pPM1002 and pPM1003.

Thus, pPM1001, pPM1002 and pPM1003 appear to be useful in the formulation of a vaccine as described by this invention.

The invention could be said to reside in the oral ingestion by man of a pharmaceutically and physiologically acceptable carrier expressing the vibrio cholerae O-antigen of the lipopolysaccharide.

In a further form, the invention could reside in the replication of bacterial strains carrying therewith a plasmid carrying the genes encoding enzymes which synthesise O-antigen.

In a further form, the invention could be said to reside in a bacterial strain providing for the expression of O-antigen of Inaba type which also has antigenic specificity shared with Ogawa type O-antigen.

In a further form, the invention could reside in a bacterial strain useful as an oral vaccine to assist in promotion of immunity in man to *Vibrio cholerae* where such bacterial strain is of a type which will invade the lymphoid tissue of the small intestine for a limited but sufficient period of time, and being a strain rendered non pathogenic such that the invasive characteristic relevant to the lymphoid tissue of the small intestine remains, the derived strain retaining the above characteristics also carrying therein genes enabling the synthesis of the O-antigen of the *Vibrio cholerae*.

The invention could reside in the method of promoting immunisation to *Vibrio cholerae* of man which comprises the oral ingestion of the said bacterial strain.

It is implicit throughout this description that the effective value of the O-antigen is such to promote immunisation or at least significant resistance to the pathogen *Vibrio cholerae*.

To assist in a further understanding of this invention there is further attached hereto analysis of materials thus far produced as set out herein in this last example.

The invention could reside in the method of preparing in the first instance appropriate DNA in which the steps of separation and concentration do not include centrifugation or extraction using pipetting or the like and includes pronase to prevent enzyme degradation of the DNA.

We have developed a procedure which allows us to rapidly isolate *Vibrio cholerae* or *Salmonella typhimurium* or 5 other bacterial DNA suitable for recombinant DNA use, without recourse to CsCl centrifugation or long incubation times.

Method

*Vibrio cholerae* strains 569B (Classical, Inaba) and 017 (El Tor, Ogawa), and *Salmonella typhimurium* LT 2 have been successfully used for purification of chromosomal DNA. The procedure is described below.

Cells were grown overnight with aeration at 37° in 20 ml of Brain-Heart infusion broth (DIFCO). The cells were then centrifuged at 5000 xg for 10 min at room temperature and washed once in TES buffer (50 mM TrisHCl, 5 MM EDTA and 50 mM NaCl pH 8.0), followed by centrifugation again, and the washed cells were then resuspended in one-tenth of the original volume (i.e., 2.0 ml) in cold 25% sucrose in 50 mM Tris-HCl pH 8.0. To this was added 1.0 ml of 10 mg/ml lysozyme in 0.25M EDTA pH 8.0, and the suspension was allowed to stand on ice for 20 min. TE bufer (10 mM Tris-HCl, 1 mm EDTA pH 8.0) (0.75 ml) was then added followed by 0.25 ml of lysis solution (5% sarkosyl, in 50 mM Tris-HCl, 0.25M EDTA pH 8.0). Solid pronase (10 mg) was also added to the mixture and gently mixed. This was incubated for 60 min at 56° with occasional shaking. Lysis becomes apparent at this time.

The lysate was then transferred to a 50 ml Ehrlenmeyer flask and gently extracted three times with phenol saturated with TE buffer (10 mm Tris-HCL, 1 m MEDTA pH 8.0). This is usually made by adding 1 g of phenol per ml of TE. The residual phenol is then removed by extracting twice with diethyl-ether. Two volumes (8 ml) of cold (15° C.) 95% ethanol were then added to the clear viscous DNA solution.

This resulted in the precipitation of a large mass of stringy DNA. This mass readily settles and the aqueous ethanol solution can be decanted since the DNA also tends to adhere to the glass. The DNA was then washed twice with 70% ethanol in a similar manner.

The washed DNA was then dried under vacuum for approximately 60 min, after which 1.0 ml of TE buffer was added and heated at 56° C. for a few minutes. The DNA solution was then transferred to a 1.5 ml Eppendorf tube and any residual particulate material removed by centrifugation for 2 min in an Eppendorf 5414 table top centrifuge. The supernatant was transferred to a fresh tube and stored at 4° C. The concentration of DNA was usually in the range of 200–500 µg/ml.

Results and Discussion

Figure 26:
FIG. 26: Analysis of chromosomal DNA by electrophoresis in 0.8% agarose in TBE buffer followed by staining with ethidium bromide and visualization using an ultra violet transilluminating light source. The following lanes are shown:
1. *Vibrio cholerae* 569B DNA uncut
2. *Salmonella typhimurium* LT2 DNA uncut
3. DNA as in 1 but digested with either Pst1 (left panel) or EcoR1 (right panel)
4. DNA as in 2 but digested with either Pst1 (left panel) or EcoR1 (right panel)
5. DNA as in 3 but ligated.
6. DNA as in 4 but ligated.

FIG. 26 shows the results obtained by restriction endonuclease digestion followed by 3 hour ligation of either *V. cholerae* or *S. typhimurium* DNA. It can be seen that the DNA could be fully cut with either EcoRl or BamHl and that upon ligation it moves back to high molecular weight material such that significant amounts remain trapped in the sample well.

The material shown has been pipetted using normal disposable tips (Gilson C20), however, if the aperture is increased by slicing off the tip with a scalpel blade the apparent molecular weight of the uncut and ligated DNA is significantly higher. It should be noted that no pipetting of the DNA is at all involved in the procedure and all manipulations are such as to minimize shearing.

The method has several advantages over the widely used method of Marmur in that only small volumes of organisms are required (20 ml) and that there are no extended or overnight incubations, indeed the whole procedure can be completed in three hours or less, yielding sufficient DNA for many cloning experiments. More recent methods involve overnight CsCl centrifugation which is time consuming and appears not to be necessary to obtain DNA of sufficient quality for molecular cloning experiments.

In addition to the use of DNA prepared by this procedure for cloning O-antigen genes, this procedure has been used in this laboratory for successfully cloning the

*Vibrio cholerae* genes for several outer membrane proteins and for haemolysin production.

The method has also been used for the construction of several *Vibrio cholerae* cosmid banks, which necessitated having restriction fragments of greater than 38 kb. There is no reason why this method should not prove successful with other gram negative organisms and has also been used successfully in our laboratory for making a cosmid bank of *Salmonella typhimurium.*

EXAMPLE 6

This example relates to the molecular cloning and expression in *Escherichia coli* K-12 of the genes that determine the O-antigen of *V. cholerae* of the Inaba form derived from strain 569B and of the Ogawa form derived from strain 017.

Materials and Methods

Bacterial strains and media. *V. cholerae* 569B and 017 were from the departmental collection. *E. coli* K-12 DHI (F$^-$gyrA96 recA1 endA1 thi-1 hsdR17 supE44$\lambda^-$) was obtained from B. Bachmann of the *E. coli* Generic Stock Center. Plasmid pHC79 was obtained from J. Collins, *V. cholerae* strains were routinely grown in brain heart infusion broth (Difco Laboratories, Detroit, Mich. ), and *E. coli* K-12 derivatives in nutrient broth (Difco) made at double strength with 5 g of NaCl per liter added. Nutrient agar was blood agar base (Difco) without the addition of blood.

Antibiotics were used at the following concentrations: ampicillin, 25 $\mu$g/ml; tetracycline, 10 $\mu$g/ml.

Chromosomal DNA preparation. Cells were grown overnight with aeration at 37° C. in 100 ml of brain heart infusion broth (Difco). The cells were then centrifuged 5,000×g for 10 min at room temperature and washed once in 20 ml of TES buffer (50 mM Tris hydrochloride, 5 mM EDTA, and 50 mM NaCl [pH 8.0]), followed by centrifugation again; and the washed cells were then suspended in 1/50th of the original volume (i.e., 20 ml) in cold 25% sucrose in 50 mM Tris hydrochloride (pH 8.0). To this was added 1.0 ml of 5 mg of lysozyme per ml in 0.25 M EDTA (pH 8.0), and the suspension was allowed to stand on ice for 10 min. To this was added 1 ml of 10 mg of pronase per ml in TE buffer (10 mM Tris hydrochloride, 1 mM EDTA [pH 8.0]). This was incubated for 10 min at 37° C. followed by the addition of 0.25 ml of lysis solution (5% Sarkosyl [CIBA-GEIGY Corp., Summit, N.J.] in 50 mM Tris hydrochloride, 0.25 M EDTA [pH 8.0]). This was incubated for 60 to 120 min at 37° C. with occasional gentle swirling. Lysis became apparent at this time. The lysate was then transferred to a 50 ml Erlenmeyer flask and gently extracted three times with phenol saturated with TE buffer (this was made by adding 1 g of phenol per ml of TE buffer). The residual phenol was then removed by extracting twice with diethyl ether. The DNA solution was then dialyzed overnight against TE buffer at 4° C. The concentration of DNA was usually in the range of 800 to 1,300 $\mu$g/ml.

Construction of cosmid gene banks. Genomic fragments of approximately 40 kilobases (kb) were obtained by controlled partial digestion with the restriction endonuclease Sau3A. The cosmid vector used was pHC79, and this was restricted with BamHI and treated with molecular biology grade alkaline phosphatase (Boehringer Mannheim Biochemicals, Sydney, Australia) to prevent self-ligation. The two DNA's were mixed, ligated overnight, and packaged in vitro into bacteriophage $\lambda$. The packaged phage were then used to infect restrictionless (hsdR), recombination deficient (recA) *E. coli* K-12 DHI. Cells harboring cosmid clones were detected by plating onto nutrient media containing ampicillin. Greater than 90% of colonies were tetracycline sensitive and could be assumed to contain *V. cholerae* DNA. Random colonies showed cosmids of between 35 and 50 kb.

Restriction analysis. Restriction endonucleases were used as described by the suppliers. Analysis of the digests was by electrophoresis on either 0.8 or 1% agarose. Usually about 0.5 $\mu$g was digested for 1 h at 37° C. in a total volume of 20 $\mu$l with 2 U of the appropriate endonuclease, either singly or in combination. Samples were run on gels (130 by 140 by 5 mm) submerged in TBE buffer (67 mM Tris base, 22 mM boric acid, 2 mM EDTA [pH 8.8]). DNA fragments were visualized on a transilluminating UV light source following staining with 2 $\mu$g of ethidium bromide per ml.

Haemagglutination inhibition assays. Sheep erythrocytes were sensitized with alkali-treated, purified LPS. To 100 $\mu$l of diluted antiserum (a polyclonal antiserum raised against heat-killed organisms and homologous to the LPS used to sensitize the sheep erythrocytes), containing 4 haemagglutination units of antibody, was added 100 $\mu$l containing twofold serial dilutions of purified LPS.

Haemagglutination trays were incubated for 60 min at 37° C., and the endpoints were determined.

Protection tests. Infant mouse protection tests were performed as described previously. Five-day-old mice were fed 20 50% lethal doses ($9.4\times10^5$ for strain 017 and $5.5\times10^5$ for strain 569B) with dilutions of antiserum. The experiment continued until the last of the controls (fed *V. cholerae* without antiserum) died.

The protective index was calculated as the reciprocal of the dilution of antiserum which gave 50% protection.

TABLE 4

Haemagglutination inhibitions

| LPS source | Amt (ug) of LPS required to inhibit haemagglutination of sheep erythrocytes sensitized with LPS from: 569B (Inaba) | 017 (Ogawa) |
|---|---|---|
| *V. cholerae* 569B (Inaba) | 0.012–0.024 | 0.78 |
| *V. cholerae* 017 (Ogawa) | 0.20 | 0.20 |
| *E. coli* K-12 DH1 (pHC79) | 100 | 100 |
| *E. coli* K-12 DH1 (pPM1001) | 0.05 | 3.1 |
| *E. coli* K-12 DH1 (pPM1003) | 0.78 | 0.78 |

Results

Molecular cloning of the O-antigen genes. We assumed that the synthesis of the O-antigen of *V. cholerae* is determined by a gene cluster, as observed in Salmonella species, and that it is genetically complex. Consequently, we used cosmid cloning and in vitro packaging into bacteriophage $\lambda$ as the means of reliably obtaining cloned fragments of sufficient size to enhance our chances of cloning the O-antigen gene cluster.

The cosmid banks were prepared (see FIG. 29) and maintained frozen at −25° C. on nitrocellulose filters on nutrient agar plates containing 25% glycerol.

Replicas of the cosmid gene banks on nitrocellulose filters were screened by colony blotting with rabbit antiserum to either live strain 569B (for the Inaba clone) or live strain 017 (for the Ogawa clones) followed by a goat-anti-rabbit-immunoglobulin G (IgG) coupled with horseradish peroxidase, as described elsewhere. About 20 strongly positive-reacting colonies from a bank of about 900 clones from 569B and 19 strongly positive-reacting colonies from 650 clones obtained from 017 were examined further.

Figure 27:
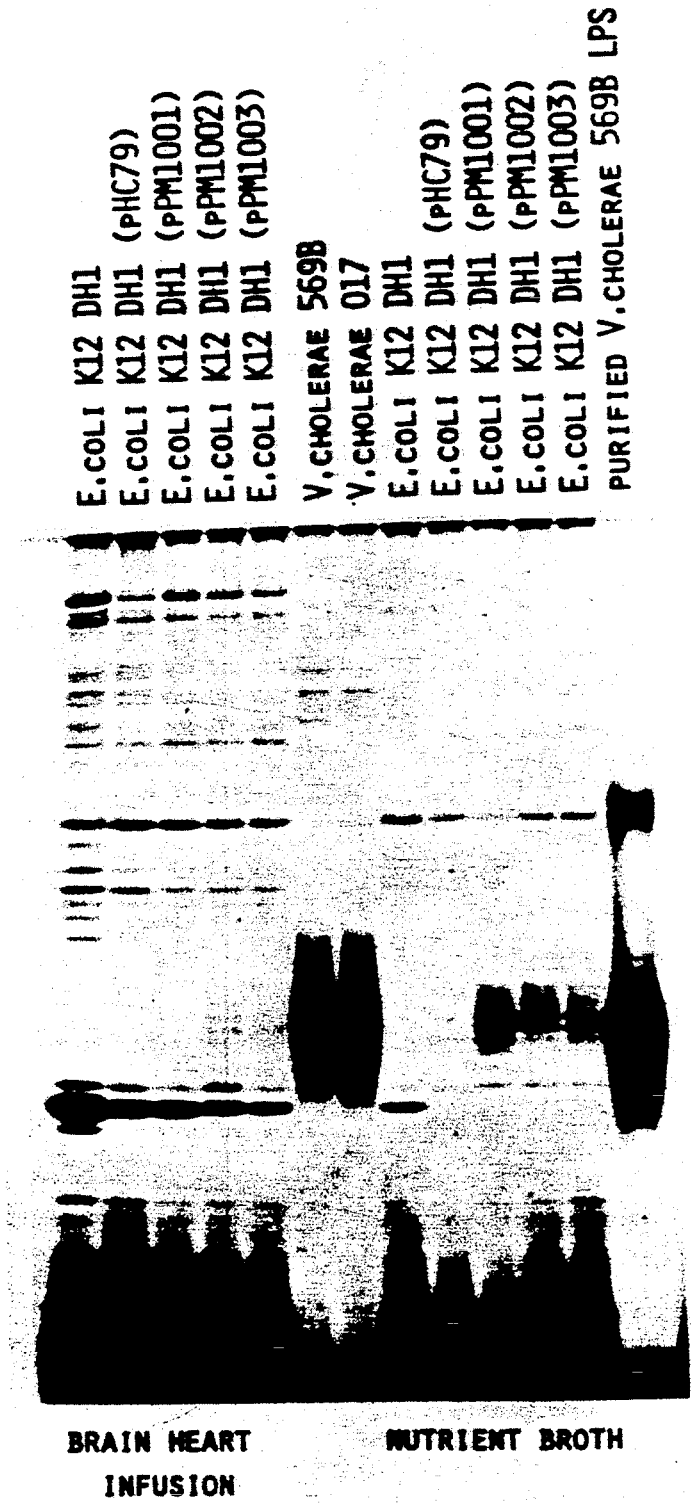
FIG. 27 presents photographs of silver stained gels. The gel were obtained by electrophoresis of the solubilized cell envelopes of bacterial strains grown in brain heart infusion broth (left panel) or nutrient broth (right panel).

Cell envelope material from these clones was prepared, solubilized in sodium dodecyl sulfate (SDS) and analyzed by SDS-polyacrylamide gel electrophoresis, followed by silver staining. Of the clones, one derived from 569B and two derived from 017 showed a pattern typical of O-antigen material (FIG. 27). These clones did not react with antisera absorbed with the homologous LPS. The plasmids in these clones were designated pPM1001 from 569B, and pPM1002 and pPM1003 from 017, respectively.

FIG. 27 illustrates cell envelopes of V. cholerae 569B and 017 and E. coli K-12 DH1 and its derivative. The E. coli K-12 derivatives were grown in either brain heart infusion broth (as were the V. cholerae strains) or nutrient broth (Difco). The envelopes prepared by the small-scale method described previously were solubilized in SDS and electrophoresed in SDS on 20% polyacrylamide gels by the method of Lugtenberg et al., as modified previously. The gels were fixed so that LPSs or lipoproteins were predominantly stained with silver.

The level of expression of O-antigen material in different growth media was highly variable. Growth in brain heart infusion broth greatly suppressed the level of expression, suggesting catabolite repression, because brain heart infusion broth is rich in sugars which are not present in nutrient broth (FIG. 27). This suppression is extreme in the case of E. coli containing pPM1001, in which O-antigen production appeared to be eliminated. The differences among pPM1001, pPM1002, and pPM1003 may reflect different regulatory regions (see below for comparison of DNA).

LPS analysis. LPS was extracted from E. coli K-12 DH1 harboring pHC79, pPM1001, or pPM1003 by the hot phenol-water method. This material was analyzed by SDA-polyacrylamide gel electrophoresis followed by silver straining and readily showed the production of a ladder of bands typical of O-antigen side chains on the LPS (FIG. 28). If this same material was transferred to nitrocellulose and Western blotted with antiserum to the V. cholerae Inaba LPS, then only this O-antigen material was recognized.

FIG. 28 illustrates comparison by SDS-gel electrophoresis on 20% polyacrylamide of LPSs from V. cholerae 569B (classical and Inaba) and 017 (El Tor and Ogawa), and E. coli K-12 DH1 harboring either the cosmid vector pHC79 or the O-antigen clones pPM1001 (Inaba) or pPM1002 and pPM1003 (Ogawa). Approximately 6 µg of LPS was loaded in each well. The gel after silver staining is shown as (A).; a duplicate gel which was electrophoretically transferred to nitrocellulose and on which a Western blot was performed with affinity-purified anti-Inaba LPS serum is shown as (B). The blot was developed with goat-anti-rabbit-IgG coupled with horseradish peroxidase.

TABLE 5

| | Infant mouse protection tests[a] | |
|---|---|---|
| | Protective index to challenge organism of: | |
| Antiserum to: | 569B (Inaba) | 017 (Ogawa) |
| V. cholerae 569B (Inaba) | 700–1,200 | ND[c] |
| V. cholerae 017 (Ogawa) | ND | 680–850 |
| E. coli K-12 DH1 (pHC79) | 10[b] | 10[b] |
| E. coli K-12 (pPM1001) | 850 | 223 |

[a]Challenge tests were performed with 20 50% lethal doses simultaneously with rabbit antisera administered orally.

Purified LPS was also compared with LPS extracted from V. cholerae in haemagglutination inhibition assays to see what concentration of LPS was capable of inhibiting the agglutination of LPS-sensitized sheep erythrocytes with a constant 4 haemagglutination units of antibody. The results (Table 5) show that the homologous serotype is better at inhibition in both cases.

The presence of plasmid pPM1001 resulted in the production of O-antigen specifically for the Inaba serotype, as judged by the amount of LPS required for inhibition, whereas pPM1003 has specificity for the Ogawa serotype. However, there was considerable cross-reaction, as was also borne out by Western blotting (FIG. 28). This was presumably due to the common A antigen because a polyclonal anti-serum to the LPS was used.

The chain length of the LPS in E. coli K-12 was similar to that observed in V. cholerae, except that there was less of the higher molecular weight forms and that shorter chain length molecules were also detected (FIG. 28). The resolution of these bands into a typical ladder pattern was marked. There appeared to be a slight shift in the average length of LPS molecules with O-antigen in E. coli K-12 (longer) compared with that in V. cholerae (shorter). This probably reflects a difference in the lengths of the respective core oligosaccharides. However, without more detailed knowledge of the core structure of V. cholerae, another possibility cannot be ruled out. It is possible that the O-antigen chains are in fact longer because of their inefficient transfer onto the E. coli K-12 core.

The results show that the enzymes involved in O-antigen biosynthesis can function in E. coli K-12, which itself has a defective rfb (O-antigen biosynthesis) region. The ability of the LPS core of E. coli to be substituted with V. cholerae O-antigen may reflect the fact that the core regions of the two organisms are related. However, the analyses demonstrate that the O-antigens being produced by E. coli K-12 are immunologically indistinguishable from those of V. cholerae.

Analysis of the cloned DNA. Plasmid pPM1001 was analyzed extensively (FIG. 29), and various deletion derivatives and subclones were obtained, none of which expressed the O-antigen. These results, together with those described below, imply that more than just the region of homology, between the three clones is required for O-antigen expression.

Figure 29:
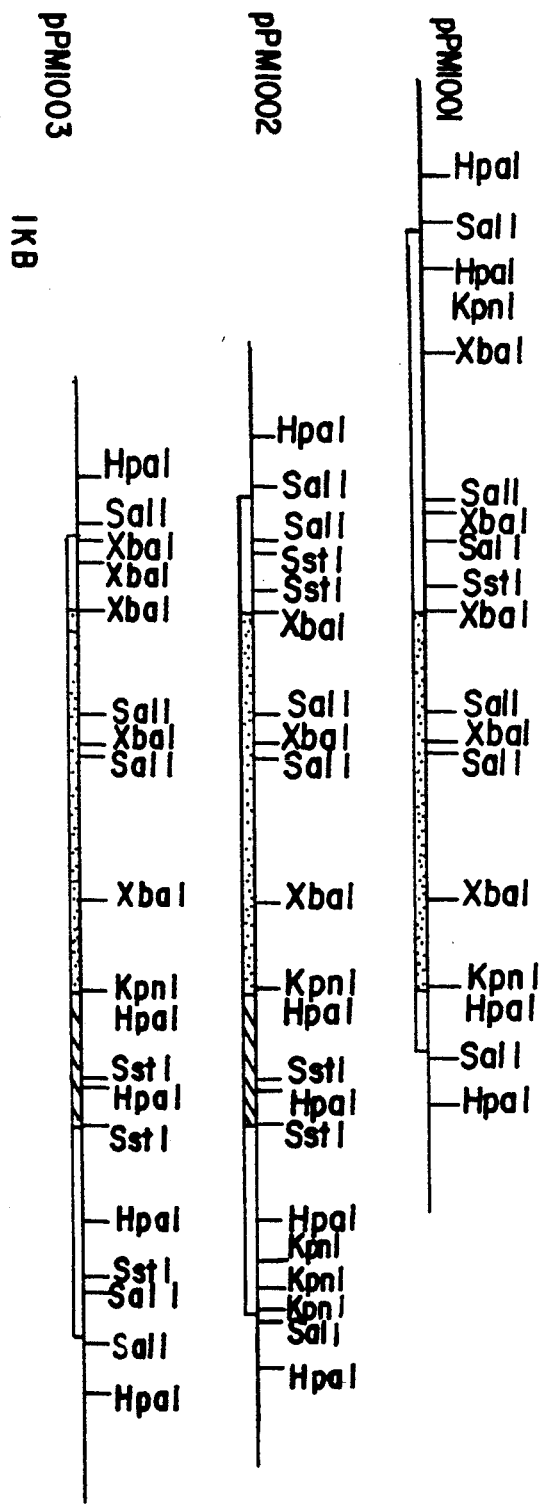
FIG. 29 provides linearized restriction maps of plasmids pPM1001, pPM1002, and pPM1003.
Figure 30:
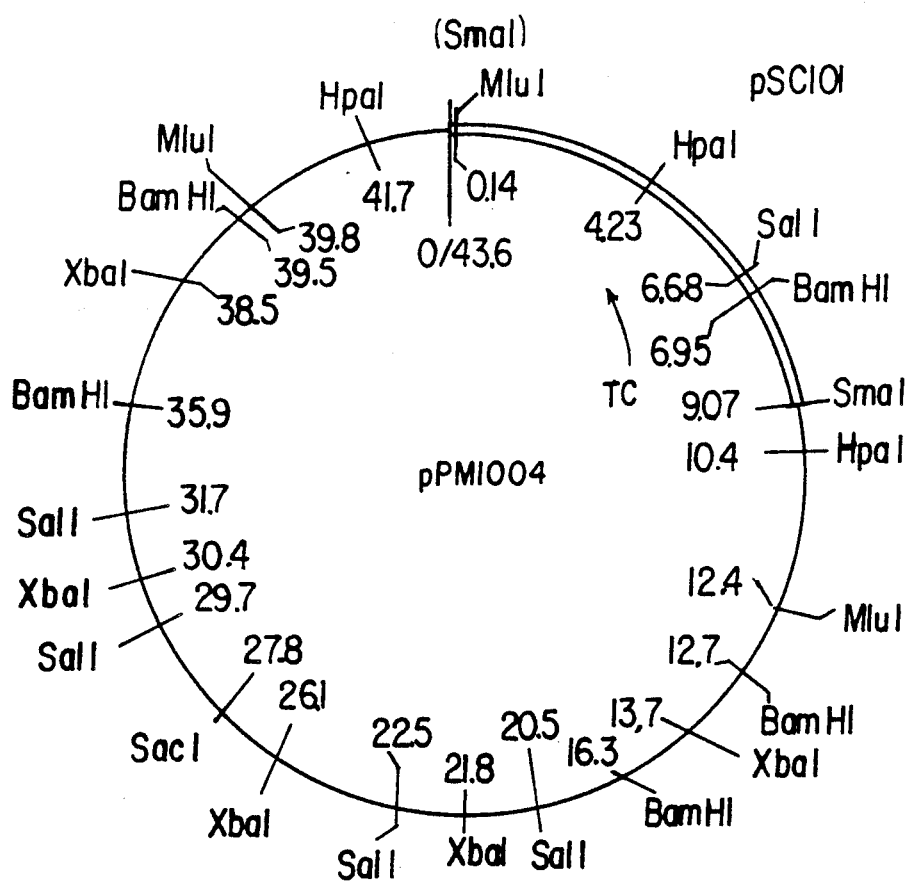
FIG. 30 is a restriction map of pPM1004.

FIG. 29 illustrates restriction analysis of the DNA contained within plasmids pPM1001 (Inaba) and pPM1002 and pPM1003 (Ogawa). The solid regions are the common DNA among all three clones; the hatched regions are DNA common to the Ogawa clones; the open regions are either nonhomologous DNA or DNA in which the extent of homology is uncertain. The thin lines correspond to the vector DNA pHC79.

Limited comparision was performed among plasmids pPM1001 and pPM1002 and pPM1003 (FIG. 29). However, there was sufficient restriction information to demonstrate that much of the DNA is identical and is flanked by regions of nonidentity. These different flanking regions probably arose during ligation because unfractionated, partially digested chromosomal DNA was used in the cloning. It can be seen that pPM1001 shares about 15 kb of DNA with pPM1002 and pPM1003 and that there is at least a further 5 kb of DNA common between the latter two Ogawa clones.

Plasmid pPM1001 posesses two large inverted repeat regions within the cloned DNA, extending outward from the central SalI sites to the HpaI sites near the ends of the cloned DNA (FIG. 29). This appears to be a cloning artifact and is not present as such on the chromosome. It was also demonstrated that the DNA at the left end of pPM1002 and at the right end in pPM1003 represents the real contiguous chromosomal DNA.

The differences observed at the DNA level may account for variation in expression between the clones on different media. For example, genes could be expressed from a vector promoter in one case and a cloned *V. cholerae* promoter in another, and these promoters could be differentially regulated.

Interestingly, all three clones had two copies of the cloning vector joined in a head-to-head fashion. Because pHC79 replicates unidirectionally, this probably serves to repress replication and reduce plasmid copy number, a phenomenon that we observed. This seems to suggest that a high gene dosage is detrimental to the cell. In fact, plasmid pPM1004, which contains the whole of the *V. cholerae* DNA in pPM1001 cloned into pSC101, a low-copy-number plasmid, is considerably more stable than pPM1001 and produces at least as much *V. cholerae* O-antigen.

More detailed analyses are in progress to determine the minimum region required for O-antigen biosynthesis, the transcriptional organization of this region, and the differences between the Inaba and Ogawa serotypes.

Protection tests. *E. coli* K-12 strains harboring either pHC79 or pPM1001 were used to immunize rabbits to produce antisera for analysis of their protective activity in the infant mouse animal model system with either *V. cholerae* 569B (Inaba) or 017 (Ogawa) as the challenge organism. The results of these experiments are summarized in Table 5. They demonstrate that antisera raised against *E. coli* K-12 harboring pPM1001 compare favourably with antisera raised similarly against *V. cholerae* 569B. That is, the O-antigen produced by *E. coli* K-12 harboring pPM1001 behaves antigenically like that produced by *V. cholerae* 569B and is highly protective in this model system, which is currently the best method available to use for testing protection.

Plasmid pPM1004

The molecular cloning of DNA encoding *V. cholerae* O-antigen, in *E. coli* K-12, has been described above. Plasmid pPM1001 contained 34 kbp of DNA from *V. cholerae* 569B (Inaba) in the cloning vector pHC79. Restriction enzyme NaeI sites were located very close to either end of this 34kbp segment, and no internal NaeI sites were evident.

Plasmid pPM1001 was cut with NaeI and ligated with SmaI-cut, alkaline phosphatase-treated vector pSC101 (single copy number, with tetracycline-resistance). After transformation into *E. coli* K-12 CGSC6040 (gyrA96, recAl, relAl, endA, thi-1 hsdR17, supE44λ, −1 with selection for tetracycline-resistance, plasmid DNA was prepared from transformants, and one strain both had a plasmid of the expected structure (named pPM1004, FIG. 30) and expressed *V. cholerae* O-antigen as judged by haemagglutination inhibition tests.

EXAMPLE 7

In this example southern hybridization analysis of chromosomal and cosmid DNA, and heteroduplex analysis between the clones have been utilised to precisely define the region of contiguous chromosomal DNA in the vicinity of the O-antigen encoding region. These data and comparison end points of clones and of deletion derivatives demonstrate that at least 16 kb of a 19 kb SstI fragment is required to encode O-antigen biosynthesis. Expression of O-antigen is independent of the orientation of this SstI fragment with respect to cloning vectors suggesting that its regulatory region has been cloned intact. No detectable differences were observed in the restriction patterns of the Inaba and Ogawa coding regions implying only minor changes are involved when serotype conversion (Inaba to Ogawa or vice versa) occurs.

Materials and Methods a) Bacterial Strains and Plasmids

*Vibrio cholerae* strains 569B (Classical, Inaba), 017 (El Tor, Ogawa) and 1633 (El Tor, Hikojima) were as described above.

The plasmids, pPM1001 (Inaba), and pPM1002 and pPM1003 (Ogawa), derived from strains 569B and 017 respectively, were as described above. Plasmid pPM1005 was a further clone expressing the Ogawa serotype and isolated from an independently constructed gene bank derived from strain 017 in the vector pHC79. These plasmids were maintained in *E. coli* K-12 strain DHl (F− gyrA96, recAl, relAl, endAl, thi-1, hsdR17, supE44, λ−). Strains were maintained as frozen glycerol cultures at −20° C. and −70° C. and lyophilized for long term storage.

b) Media

*V. cholerae* strains were routinely grown in Brain Heart Infusion broth (DIFCO) and the *E. coli* K-12 derivatives in nutrient broth (DIFCO) made at 16 g with 5 g NaCl per litre added.

c) Plasmid Preparation

Plasmid DNA was prepared by standard methods. DNA was centrifuged on CsCl-EtBr gradients. Two centrifugations were done; the first for 18 hours at 50,000 r.p.m., in a Beckman 60 Ti rotor. The plasmid band was removed and recentrifuged for 18 hours at 50,000 r.p.m. in an 80 Ti rotor.

d) Restriction Endonuclease Analysis

Restriction endonucleases were used as directed by the suppliers. Digests were analyzed on 0.6% or 0.8% agarose gels; usually about 0.5 μg of DNA was digested with two units of restriction endonuclease in a total volume of 20 ml. Samples were run using TBE buffer. DNA fragments were visualized on a transilluminating UV light source after staining with 2 μg Et Br/ml in water.

e) Southern DNA Hybridizations

DNA hybridization analysis of plasmids and whole genomic DNA was performed using the procedure of Southern (1975).

f) Bacterial Agglutinations

Exponential phase bacteria ($4 \times 10^8$ cells/ml) were washed and resuspended to a density of $10^{10}$ cells/ml in saline. An equal volume of cells (100 µl) was added to two-fold serial dilutions of antiserum diluted in saline, in a 96-well microtitre tray. After vortexing, the tray was incubated for 120 minutes at 30° C. and then overnight at 4° C. Agglutination was scored at this time.

g) Haemagglutination Inhibition

Four haemaglutinating units (HU) of antiserum in 25 µl were mixed in the wells of a microtitre tray with an equal volume of 2-fold serial dilutions of cell envelope material (at 2 mg/ml). After mixing for 60 minutes at 37° C. sheep RBCs sensitized with the appropriate LPS were added. The trays were mixed and incubated for a further 60 minutes at 37° C. before reading.

h) Antisera

Monoclonal antibodies (MCA) were raised from the hybridoma 13-B generated after immunization with *V. cholerae* strain 569B (Inaba). The cells were injected intraperitoneally into Balb/C mice after priming with pristene. The cells were passaged every two weeks and the ascites fluid collected by peritoneal washout. Previous experiments have shown that the MCA produced by 13-B is directed against an antigen present in large amounts on Inaba strains but only in small amounts on Ogawa cells. Presumably, this could correspond to the "C" antigen associated with the Inaba serotype.

A second MCA directed against the Ogawa specific antigen (B) was also obtained.

i) Cell Envelope Preparations

Cell envelopes were prepared after breaking the cells in an Aminco-French pressure cell, according to known methods. Envelopes were resuspended in phosphate buffered saline.

j) Electron Microscopy

DNA hybridization and spreading was performed according to known methods.

k) SDS-Polyacrylamide Gel Electrophoresis (SDS-PAGE)

SDS-PAGE was performed on 11-20% polyacrylamide gradients.

l) Silver Staining

Polyacrylamide gels were stained to visualize lipopolysaccharides.

Results and Discussion

Figure 31:
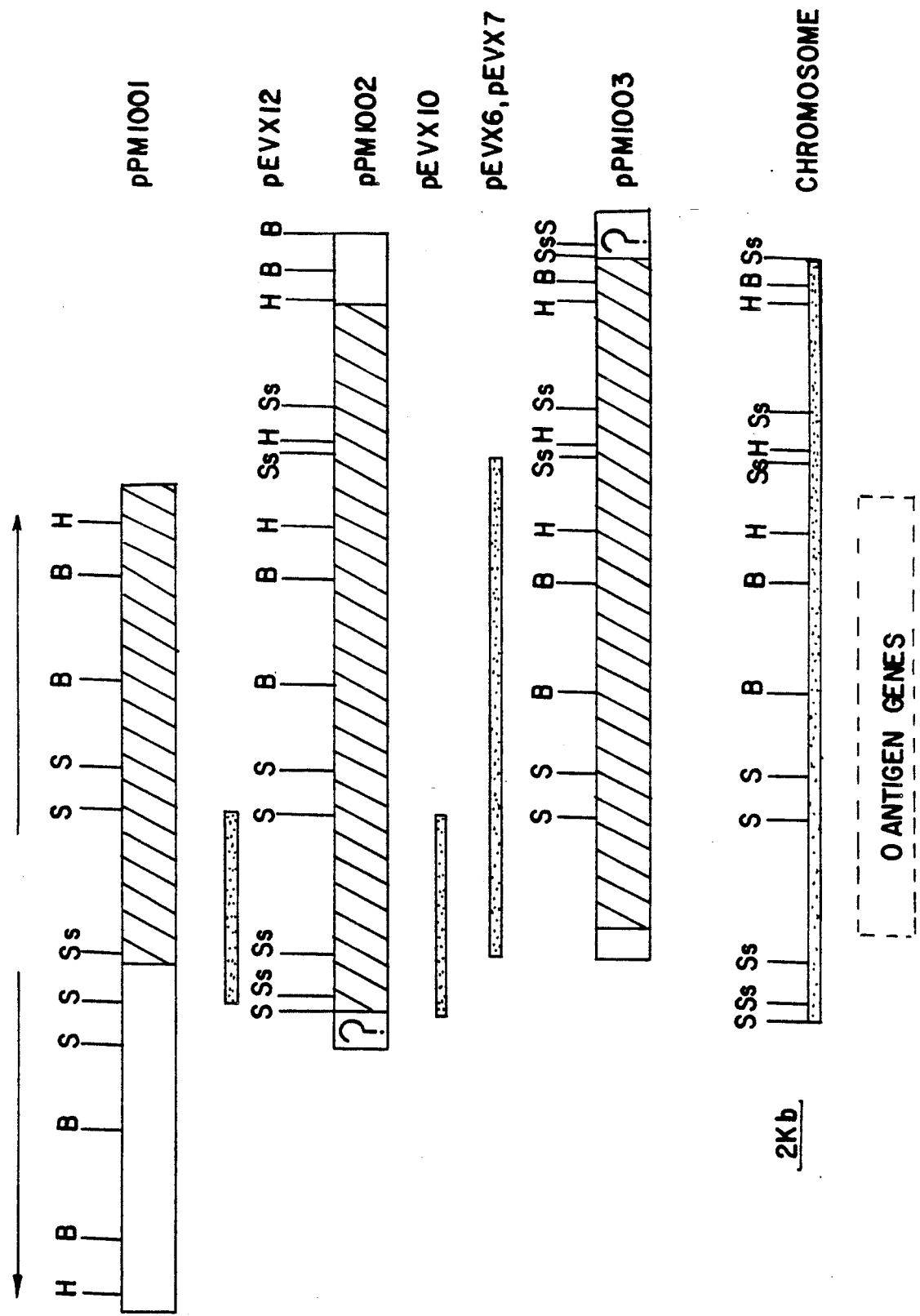
FIG. 31 compares the chromosomal DNA of *Vibrio cholerae* in the region encoding the biosynthesis of the O-antigen of the liposaccharide with various inserts in pPM1001, pEVX12, pPM1002, pEVX10, pEVX6, pEVX7, and pPM1003.

The restriction analysis described in example 7 of the cosmid clone pPM1001, expressing the Inaba serotype, suggested the presence of large inverted repeat regions which were not detected in the Ogawa clones pPM1002 and pPM1003 (see FIG. 31). Consequently we were interested in determining the chromosomal organization because of the implications such repeats had on the mechanism of serotype conversion in *V. cholerae*.

(a) Serotyping of *E. coli* K-12 Harbouring the Various Clones

The haemagglutination inhibition assay (Table 4) results clearly differentiate pPM1001 and, pPM1002 and pPM1003 as Inaba and Ogawa, respectively. The difference between pPM1002 and pPM1003 was reproducible and probably reflects differences in the relative amounts of the B antigenic determinant present in the cell envelopes of *E. coli* K-12 harbouring these plasmids. Alternatively, it could imply that there is less of the particular Ogawa determinant, possible 4-amino-4-deoxy-L-arabinose, substituted onto the LPS in strains containing pPM1003.

(b) Homoduplex Analysis of Plasmids pPM1001, pPM1002, pPM1003 and pPM1005

Homoduplex analysis (i.e., intrastrand annealing) of plasmids pPM1001, pPM1002, pPM1003 and pPM1005 demonstrated that each plasmid possessed two copies of the cloning vector pHC79 in a head to head arrangement. Only pPM1001 demonstrated extensive inverted repeats as predicted by restriction enzyme analysis.

Since pHC79 is a pBR322 derivative and replicates unidirectionally, each copy of the vector will be working against the other and is probably the reason for the low copy number observed.

c) Heteroduplex Analysis between pPM1001, pPM1002 and pPM1003, and their Derivatives Heteroduplex analyses have been performed using pPM1001 and pPM1002, pPM1001 and pPM1003 and pPM1003 in order to see how much of the DNA these plasmids had in common. In addition plasmids pPEVX12 and pEVX10 which contain the central SalI fragments of pPM1001 and pPM1002 respectively subcloned into pACYC184 (see FIG. 31) were also compared. Where ambiguity could arise regarding plasmid identity, additional heteroduplexes were performed in which one of the plasmids was pretreated with a suitable restriction endonuclease. These experiments enabled the limit of homology to be defined.

Two questions arise from these analyses: Is the inverted repeat arrangement present in the chromosome? What DNA, present in the clones corresponds to the contiguous chromosomal DNA? We have sought to answer these questions by Southern hybridization analysis.

(d) Southern Hybridization Analysis

Plasmid pEVX12 DNA has been used to probe whole genomic DNA of *V. cholerae* and plasmids pPM1001, pPM1002 and pPM1003. Plasmid pEVX12 was used because the previous example showed that at least a part of this region was homologous in all three plasmids.

Figure 32:
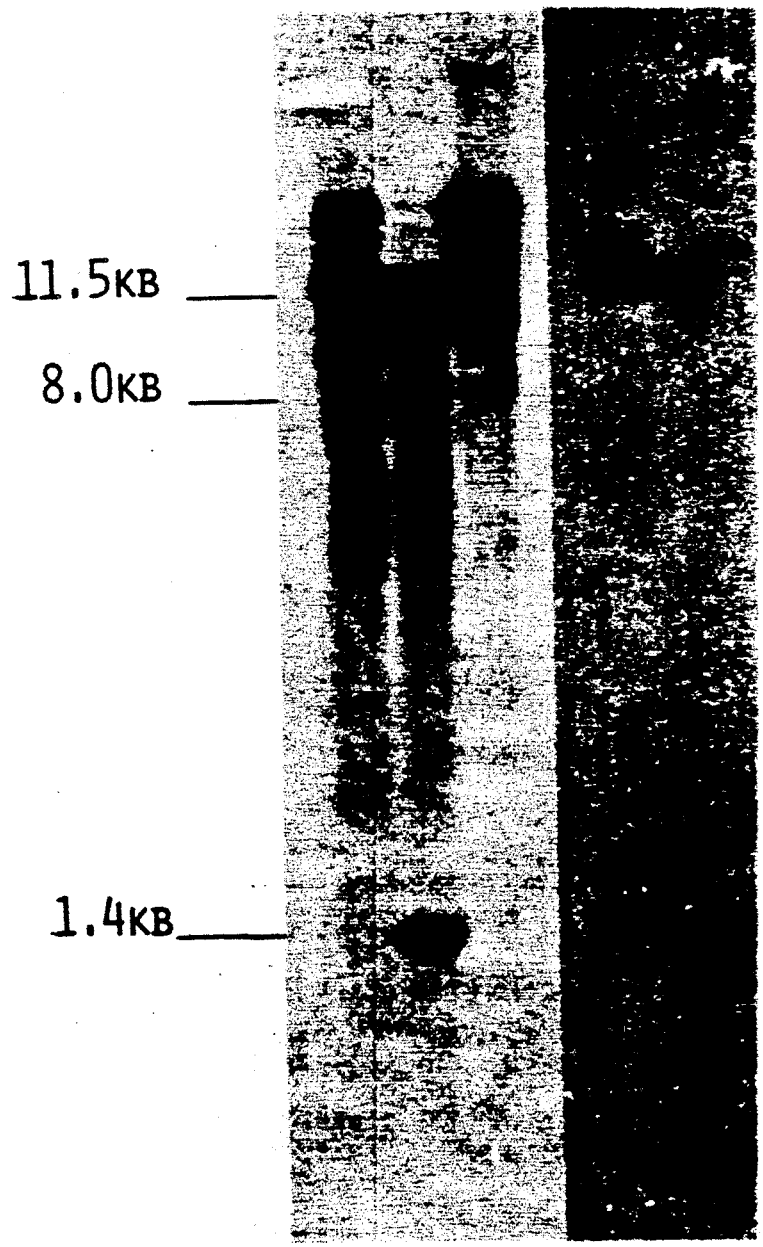
FIG. 32 presents a southern hybridization analysis of whole genomic DNA of *V. cholerae* strains 569B and 017, and of plasmids pPM1001, pPM1002 and pPM1003, using plasmid pEVX12 DNA as a probe.

The three DNAs were digested with both BamHI and SstI since these enzymes will give asymmetric fragments of about 8 and 11.5 kb if the arrangement in pPM1001 were real. The results (FIG. 32) show that only the 11.5 kb fragment could be detected in the chromosome as well as in plasmid pPM1002. This implies that the 8 kb fragment is a hybrid from at least two other fragments, indicating that the inverted repeat arrangement in pPM1001 is a cloning artefact. It was not detected in pPM1003 which has neither the SstI site, nor DNA homologous to pPM1002 in this region.

An additional fragment of 1.4 kb corresponding to the small SstI fragment at the left end of pPM1002 was detected confirming this to be also contiguous DNA in the chromosome. Southern analyses of chromosomal DNA digested with SstI using either whole pPM1002 or pPM1003 as a probe indicated the SstI fragments of 1.8 and 6.0 kb at the right of pPM1003 also represented contiguous chromosomal DNA. Further analyses (data not shown) using other smaller fragments only serve to confirm the map of the chromosome derived here (FIG. 31). None of these experiments provide an explanation for the structure of pPM1001 which remains a cloning artefact.

(e) O-Antigen Expression

Figure 33:
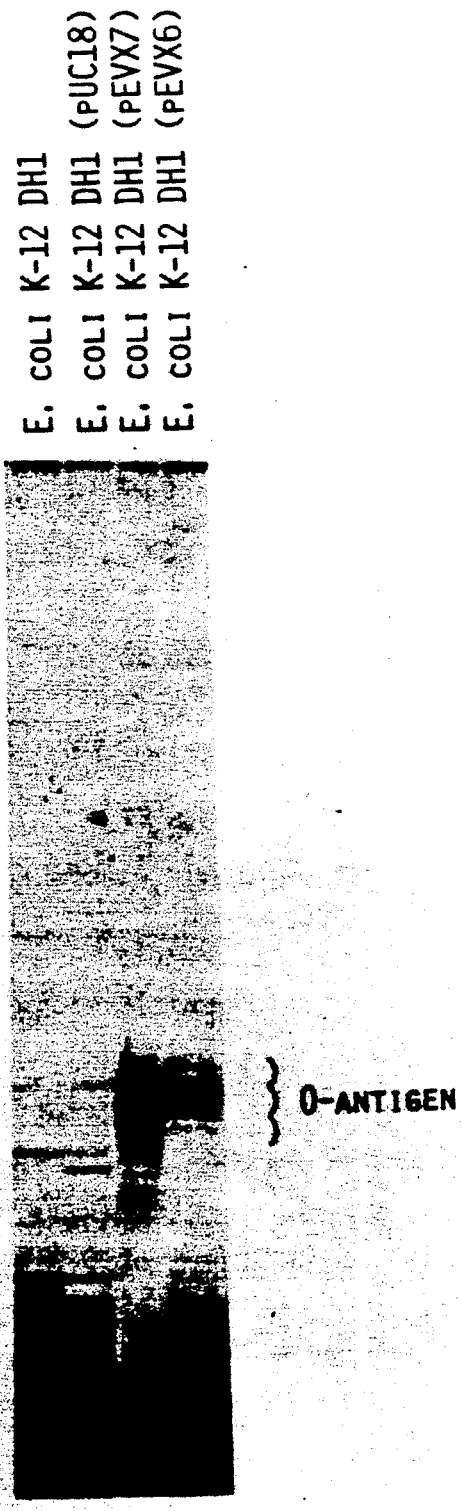
FIG. 33 is a comparison of O-antigen expression in *E. coli* K-12 DH1, and the same strain harbouring pUC18, pEVX7 or pEVX6.

Deletion analysis and subclones of pPM1001 demonstrate (not shown) that more than the large SstI-HpaI fragment, is required for expression of the Inaba serotype. Plasmid pPM1006, in which the small SstI fragments of pPM1003 were deleted, is still capable of expressing the Ogawa serotype and thus one would predict that the large SstI fragment of pPM1002 contains all the coding information for O-antigen biosynthesis. This fragment has been cloned in opposite orientations into the SstI site of pUC18 to give plasmids pEVX6 and pEVX7 (FIG. 31). In FIG. 33 it can be seen that both encode production of O-antigen although the orientation in pEVX7 leads to higher levels in the cell envelopes. This would suggest that the regulatory region of the O-antigen genes is intact and that there is an additive effect on expression due to the lac promoter in this orientation.

Together these data have enabled us to derive FIG. 31 where we present a physical map of the contiguous chromosomal DNA of *Vibrio cholerae* 01 in the vicinity of the region, encoding the biosynthesis of the O-antigen of the lipopolysaccharide.

Comparison of the end points of the DNA in the various plasmids capable of expressing O-antigen biosynthesis implies a coding region of between 16 and 19 kb contained within the single SstI fragment.

This region corresponds to oag as defined by Bhaskaran (1959), however, it would appear that in accordance with the established convention it should be designated rfb.

We claim:

1. An avirulent strain of *E. coli* comprising DNA encoding proteins which control the synthesis of the O-antigen, which DNA is derived from a *Vibrio cholerae* strain of the Inaba or Ogawa serotype, and is at least 16 kb in length.

2. An avirulent strain according to claim 1 wherein the *E. coli* strain is an *E. coli* K-12 strain.

3. An avirulent strain according to claim 2 wherein the fragment is, or is derived from a Sst/SacI fragment of approximately 19 kb in length.

4. An avirulent strain of *E. coli* comprising DNA encoding proteins which control the synthesis of the O-antigen; which DNA is borne by a cosmid selected from the group consisting of cosmids pPM1001 and pPM1004, derived from a *Vibrio cholerae* strain of the Inaba serotype.

5. An avirulent strain of *E. coli* comprising DNA encoding proteins which control the synthesis of the O-antigen, which DNA is borne by a cosmid selected from the group consisting of cosmids pPM1002, pPM1003 and pPM1005, derived from a *Vibrio cholerae* strain of the Ogawa serotype.

6. A cosmid including
(a) a suitable cosmid cloning vector; and
(b) a cloned DNA containing genes encoding proteins which control the synthesis of the O-antigen, which DNA is derived from a *Vibrio cholerae* strain of the Inaba or Ogawa serotype and is at least 16 kb in length.

7. A cosmid according to claim 6 wherein the cosmid cloning vector is cosmid pHC79.

8. A cosmid according to claim 7 wherein the cloned DNA is or is cloned from a Sst/SacI fragment of approximately 19 kb in length.

9. A cosmid including
(a) a suitable cosmid cloning vector; and
(b) a cloned DNA containing genes encoding proteins which control the synthesis of the O-antigen, which DNA is derived from a *Vibrio cholerae* strain and is at least 16 kb in length; which cosmid is selected from the group consisting of cosmids pPM1001 and pPM1004, derived from a *Vibrio cholerae* strain of the Inaba serotype.

10. A cosmid including
(a) a suitable cosmid cloning vector; and
(b) a cloned DNA containing genes encoding proteins which control the synthesis of the O-antigen, which DNA is derived from a *Vibrio cholerae* strain and is at least 16 kb in length; which cosmid is selected from the group consisting of cosmids pPM1002, pPM1003 and pPM1005, derived from a *Vibrio cholerae* strain of the Ogawa serotype.

11. A method for preparing an avirulent strain of *E. coli* comprising DNA encoding proteins which control the synthesis of the O-antigen, which DNA is derived from a *Vibrio cholerae* strain of the Inaba or Ogawa serotype, and is at least 11 kb in length, which method comprises,
providing a sample of an *E. coli* strain and a cosmid including
(a) a suitable cosmid cloning vector; and
(b) a cloned DNA containing genes encoding proteins which control the synthesis of the O-antigen, which DNA is derived from a *Vibrio cholerae* strain of the Inaba or Ogawa serotype and is at least 16 kb in length;
cloning DNA from the cosmid into the *E. coli* strain; and
isolating the avirulent strain of *E. coli* so formed.

12. A method according to claim 11 wherein an avirulent strain of *E. coli* is an *E. coli* K-12 strain.

13. A method according to claim 12 wherein the cosmid cloning vector is cosmid pHC79.

14. A method according to claim 13 wherein the cloned DNA is a Sst/SacI fragment of approximately 19 kb in length.

15. A method for preparing an avirulent strain of *E. coli* comprising DNA containing genes encoding proteins which control the synthesis of the O-antigen, which DNA is derived from a *Vibrio cholerae* strain of the Inaba or Ogawa serotype, and is at least 16 kb in length;
providing a sample of an *E. coli* strain; and a cosmid selected from the group consisting of cosmids pPM1001 and pPM1004, derived from a *Vibrio cholerae* strain of the Inaba serotype;
cloning the DNA from the cosmid into the *E. coli* strain; and
isolating the avirulent strain of *E. coli* so formed.

16. A method for preparing an avirulent strain of *E. coli* comprising DNA encoding proteins which control the synthesis of the O-antigen, which DNA is derived from a *Vibrio cholerae* strain of the Inaba or Ogawa serotype, and is at least 11 kb in length;

providing a sample of an *E. coli* strain and;

a cosmid selected from the group consisting of cosmids pPM1002, pPM1003 and pPM1005, derived from a *Vibrio cholerae* strain of the Ogawa serotype;

cloning the DNA from the cosmid into the *E. coli* strain; and isolating the avirulent strain of *E. coli* so formed.

* * * * *